United States Patent
Nguyen et al.

(10) Patent No.: US 10,253,352 B2
(45) Date of Patent: Apr. 9, 2019

(54) METHODS FOR DETERMINING SEQUENCE PROFILES

(71) Applicant: Omniome, Inc., San Diego, CA (US)

(72) Inventors: Michael Nguyen, San Diego, CA (US); Eugene Tu, San Diego, CA (US)

(73) Assignee: OMNIOME, INC., San Diego, CA (US)

( * ) Notice: Subject to any disclaimer, the term of this patent is extended or adjusted under 35 U.S.C. 154(b) by 258 days.

(21) Appl. No.: 15/354,941

(22) Filed: Nov. 17, 2016

(65) Prior Publication Data

US 2017/0137873 A1 May 18, 2017

Related U.S. Application Data

(60) Provisional application No. 62/256,461, filed on Nov. 17, 2015.

(51) Int. Cl.
*C12Q 1/68* (2018.01)
*C12Q 1/6827* (2018.01)
*C12Q 1/6888* (2018.01)

(52) U.S. Cl.
CPC ......... *C12Q 1/6827* (2013.01); *C12Q 1/6888* (2013.01)

(58) Field of Classification Search
CPC ............ C12Q 1/6827; C12Q 2525/151; C12Q 2533/101; C12Q 1/6888
USPC ...................................................... 435/91.2
See application file for complete search history.

(56) References Cited

U.S. PATENT DOCUMENTS

| | | | |
|---|---|---|---|
| 5,641,658 A | 6/1997 | Adams et al. | |
| 5,843,660 A | 12/1998 | Schumm et al. | |
| 6,221,598 B1 | 4/2001 | Schumm et al. | |
| 6,479,235 B1 | 11/2002 | Sprecher et al. | |
| 7,008,771 B1 | 3/2006 | Sprecher et al. | |
| 7,057,026 B2 | 6/2006 | Barnes et al. | |
| 7,115,400 B1 | 10/2006 | Adessi et al. | |
| 7,264,934 B2 | 9/2007 | Fuller et al. | |
| 7,790,418 B2 | 9/2010 | Mayer | |
| 8,580,505 B2 | 11/2013 | Wang et al. | |
| 8,632,975 B2 | 1/2014 | Vander Horn et al. | |
| 9,279,154 B2 | 6/2016 | Previte et al. | |
| 2002/0055100 A1 | 5/2002 | Kawashima et al. | |
| 2004/0002090 A1 | 1/2004 | Mayer et al. | |
| 2004/0096853 A1 | 5/2004 | Mayer | |
| 2005/0100900 A1 | 5/2005 | Kawashima et al. | |
| 2006/0188901 A1 | 8/2006 | Barnes et al. | |
| 2006/0240439 A1 | 10/2006 | Smith et al. | |
| 2006/0281109 A1 | 12/2006 | Barr Ost et al. | |
| 2007/0099208 A1 | 5/2007 | Drmanac et al. | |
| 2007/0128624 A1 | 6/2007 | Gormley et al. | |
| 2007/0166705 A1 | 7/2007 | Milton et al. | |
| 2008/0009420 A1 | 1/2008 | Schroth et al. | |
| 2009/0142764 A1 | 6/2009 | Hennessy et al. | |
| 2009/0286245 A1* | 11/2009 | Bjornson | C12Q 1/6869 435/6.18 |
| 2011/0306505 A1 | 12/2011 | Chang et al. | |
| 2011/0312529 A1* | 12/2011 | He | C12Q 1/6874 506/9 |
| 2012/0122093 A1 | 5/2012 | Hennessy et al. | |
| 2012/0295262 A1 | 11/2012 | Ronaghi et al. | |
| 2012/0309637 A1 | 12/2012 | Schumm et al. | |
| 2013/0165328 A1* | 6/2013 | Previte | C12Q 1/6874 506/2 |
| 2014/0065613 A1 | 3/2014 | Bormann Chung et al. | |
| 2014/0234853 A1* | 8/2014 | Vander Horn | C12Q 1/6827 435/6.19 |
| 2017/0022553 A1 | 1/2017 | Vijayan et al. | |
| 2018/0112257 A1* | 4/2018 | Ju | G01N 33/48721 |

FOREIGN PATENT DOCUMENTS

| WO | 91006678 | 5/1991 |
|---|---|---|
| WO | 2004018497 | 3/2004 |
| WO | 2005065814 | 7/2005 |
| WO | 2006/064199 | 6/2006 |
| WO | 2007/010251 | 1/2007 |
| WO | 2007123744 | 11/2007 |
| WO | 2009145820 | 12/2009 |
| WO | 2014039997 | 3/2014 |
| WO | 2014114665 | 7/2014 |

OTHER PUBLICATIONS

Chen et al., "The History and Advances of Reversible Terminators Used in New Generations of Sequencing Technology", Genomics Proteomics Bioinformatics, 11(1), Feb. 1, 2013, pp. 34-40.
Roettger et al., "Mismatched and Matched dNTP Incorporation by DNA Polymerase β Proceed via Analogues Kinetic Pathways", Biochemistry, 47, Sep. 16, 2008, pp. 9718-9727.
Tsai et al., "Site-specific labeling of T7 DNA polymerase with a conformationally sensitive flurophore and its use in Detecting single-nucleotide polymorphisms", Analytical Biochemistry, vol. 384, No. 1, Academic Press Inc., New York, Jan. 1, 2009, pp. 136-144.
PCT/US2016/062613, "International Preliminary Report on Patentability", dated May 31, 2018, 9 pages.
Ausubel et al., "Current Protocols in Molecular Biology", 1994-1998, John Wiley & Sons Publisher, vol. 1 & 2.
Burckhardt, "Amplification of DNA from Whole Blood", PCR Methods and Applications, vol. 3, 1994, 329-243.
Comey et al., "DNA Extraction Strategies for Amplified Fragment Length Polymorphism Analysis", J Forensic Sci, vol. 39, No. 5, Sep. 1994, 1254-1269.
Fuller et al., "The challenges of sequencing by synthesis", Nature Biotechnology, vol. 27, No. 11, Nov. 2009, pp. 1013-1023.

(Continued)

*Primary Examiner* — Cynthia B Wilder
(74) *Attorney, Agent, or Firm* — Kilpatrick Townsend & Stockton LLP

(57) ABSTRACT

Provided herein are methods for analyzing a signature sequence in a nucleic acid sample by rapid sequencing of a target nucleic acid region. The method examines the target nucleic acid directly and minimizes the number of examination steps needed to determine a signature that is characteristic of a genetic feature of the nucleic acid sample.

20 Claims, 10 Drawing Sheets

Specification includes a Sequence Listing.

(56) References Cited

OTHER PUBLICATIONS

Hares, "Selection and implementation of expanded CODIS core loci in the United States", Forensic Sci. Int. Genet., vol. 17, 2015, 33-34.

Ion Torrent, "Ion Torrent Amplicon Sequencing", Internet, Available at http://www.iontorrent.com/lib/images/PDFs/amplicon_application_note_040411.pdf, Apr. 4, 2011, pp. 1-5.

Lizardi et al., "Mutation detection and single-molecule counting using isothermal rolling-circle amplification", Nature Genetics, vol. 19, 1998, 225-232.

Mashayekhi, "Analysis of read length limiting factors in Pyrosequencing chemistry", Analytical Biochemistry, vol. 363, No. 2, Apr. 15, 2007, pp. 275-287.

Mccabe, "Utility of PCR for DNA analysis from dried blood spots on filter paper blotters", PCR Methods and Applications, vol. 1, 1991, 99-106.

Miller et al., "A simple salting out procedure for extracting DNA from human nucleated cells", Nucl Acids Res, vol. 16, No. 3, 1988, 1215.

Nordvåg et al., "Direct PCR of washed blood cells", Biotechniques, 1(4), 1992, 490-492.

PCT/US2016/062613, "International Search Report and Written Opinion", dated Mar. 13, 2017, 16 pages.

Petrie et al., "Deep sequencing analysis of mutations resulting from the incorporation of dNTP analogs", Nucleic Acids Res. 38(22), 2010, 8095-8104.

Santoso et al., "Conformational transitions in DNA polymerase I revealed by single-molecule FRET", Proceedings of the National Academy of Sciences, vol. 107, No. 2, Jan. 12, 2010, pp. 715-720.

Walsh et al., "Chelex 100 as a medium for simple extraction of DNA for PCR-based typing from forensic material", Biotechniques, vol. 10(4), 1991, 506-513.

Wilhelmsson, "Fluorescentnucleic acid base analogues", Quarterly Reviews of Biophysics 43, 2, 2010, 159-183.

\* cited by examiner

| Allele | sequence | repeat | |
|---|---|---|---|
| CSF1PO | AGAT | 5 | 16 |
| FGA | CTTT | 7 | 19 |
| TH01 | AATG | 3 | 12 |
| TPOX | AATG | 6 | 14 |
| VWA | TCTA | 3 | 17 |
| D3S1358 | AGAT | 8 | 20 |
| D5S818 | AGAT | 7 | 16 |
| D7S820 | GATA | 5 | 15 |
| D8S1179 | TATC | 7 | 20 |
| D13S317 | GATA | 5 | 16 |
| D16S539 | GATA | 5 | 15 |
| D18S51 | GAAA | 7 | 27 |
| D21S11 | [TCTA], [TCTG] | complex | |

| Position | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| X allele | A | G | A | T | | | | | | | G | T | T | T | C | T | C | A | A |
| Y allele | A | A | A | T | A | A | A | G | T | G | G | T | T | T | C | T | C | A | A |

*FIG. 5C*

SEQUENCE LISTING

<160> NUMBER OF SEQ ID NOS: 62

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
aacctgagtc tgccaaggac tagc         24

<210> SEQ ID NO 2
<211> LENGTH: 24

```
<212> TYPE: DNA
<213> ORGANISM: Artificial Sequence
<220> FEATURE:
<223> OTHER INFORMATION: Synthetic Construct

<400> SEQUENCE: 2
ttccacacac cactggccat cttc                                            24

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
ccggaggtaa aggtgtctta aagt                                            24

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
atttcctgtg tcagaccctg tt                                              22

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
ggctgcaggg cataacatta                                                 20

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
attctatgac tttgcgcttc agga                                            24

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
attcaaaggg tatctgggct ctgg                                            24

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8
```

-continued

```
gtgggctgaa aagctcccga tat                                        23

<210> SEQ ID NO 9
<211> LENGTH: 24
<212> TYPE: DNA
<213> ORGANISM: Artificial Sequence
<220> FEATURE:
<223> OTHER INFORMATION: Synthetic Construct

<400> SEQUENCE: 9
actggcacag aacaggcact tagg                                       24

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
actggcacag aacaggcact tagg                                       24

<210> SEQ ID NO 11
<211> LENGTH: 33
<212> TYPE: DNA
<213> ORGANISM: Artificial Sequence
<220> FEATURE:
<223> OTHER INFORMATION: Synthetic Construct

<400> SEQUENCE: 11
gccctagtgg atgataagaa taatcagtat gtg                             33

<210> SEQ ID NO 12
<211> LENGTH: 30
<212> TYPE: DNA
<213> ORGANISM: Artificial Sequence
<220> FEATURE:
<223> OTHER INFORMATION: Synthetic Construct

<400> SEQUENCE: 12
ggacagatga taaatacata ggatggatgg                                 30

<210> SEQ ID NO 13
<211> LENGTH: 15
<212> TYPE: DNA
<213> ORGANISM: Artificial Sequence
<220> FEATURE:
<223> OTHER INFORMATION: Synthetic Construct

<400> SEQUENCE: 13
actgcagtcc aatct                                                 15

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
atgaaatcaa cagaggcttg                                            20

<210> SEQ ID NO 15
<211> LENGTH: 19
<212> TYPE: DNA
<213> ORGANISM: Artificial Sequence
```

<220> FEATURE:
<223> OTHER INFORMATION: Synthetic Construct

<400> SEQUENCE: 15
actgcagtcc aatctgggt                                                   19

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16
atgaaatcaa cagaggcttg c                                                21

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
ggtgattttc ctctttggta tcc                                              23

<210> SEQ ID NO 18
<211> LENGTH: 26
<212> TYPE: DNA
<213> ORGANISM: Artificial Sequence
<220> FEATURE:
<223> OTHER INFORMATION: Synthetic Construct

<400> SEQUENCE: 18
agccacagtt tacaacattt gtatct                                           26

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
gggtgatttt cctctttggt                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
tgattccaat catagccaca                                                  20

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
atgttggtca ggctgactat g                                                21

```
<210> SEQ ID NO 22
<211> LENGTH: 24
<212> TYPE: DNA
<213> ORGANISM: Artificial Sequence
<220> FEATURE:
<223> OTHER INFORMATION: Synthetic Construct

<400> SEQUENCE: 22
gattccacat ttatcctcat tgac                                          24

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct

<400> SEQUENCE: 23
tgtcatagtt tagaacgaac taacg                                         25

<210> SEQ ID NO 24
<211> LENGTH: 23
<212> TYPE: DNA
<213> ORGANISM: Artificial Sequence
<220> FEATURE:
<223> OTHER INFORMATION: Synthetic Construct

<400> SEQUENCE: 24
ctgaggtatc aaaaactcag agg                                           23

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
tttttgtatt tcatgtgtac attcg                                         25

<210> SEQ ID NO 26
<211> LENGTH: 25
<212> TYPE: DNA
<213> ORGANISM: Artificial Sequence
<220> FEATURE:
<223> OTHER INFORMATION: Synthetic Construct

<400> SEQUENCE: 26
cgtagctata attagttcat tttca                                         25

<210> SEQ ID NO 27
<211> LENGTH: 32
<212> TYPE: DNA
<213> ORGANISM: Artificial Sequence
<220> FEATURE:
<223> OTHER INFORMATION: Synthetic Construct

<400> SEQUENCE: 27
attgcaactt atatgtattt ttgtatttca tg                                 32

<210> SEQ ID NO 28
<211> LENGTH: 28
<212> TYPE: DNA
<213> ORGANISM: Artificial Sequence
<220> FEATURE:
<223> OTHER INFORMATION: Synthetic Construct
```

<400> SEQUENCE: 28
accaaattgt gttcatgagt atagtttc					28

<210> SEQ ID NO 29
<211> LENGTH: 26
<212> TYPE: DNA
<213> ORGANISM: Artificial Sequence
<220> FEATURE:
<223> OTHER INFORMATION: Synthetic Construct

<400> SEQUENCE: 29
attacagaag tctgggatgt ggagga					26

<210> SEQ ID NO 30
<211> LENGTH: 19
<212> TYPE: DNA
<213> ORGANISM: Artificial Sequence
<220> FEATURE:
<223> OTHER INFORMATION: Synthetic Construct

<400> SEQUENCE: 30
ggcagcccaa aaagacaga					19

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
acagaagtct gggatgtgga					20

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
gcccaaaaag acagacagaa					20

<210> SEQ ID NO 33
<211> LENGTH: 24
<212> TYPE: DNA
<213> ORGANISM: Artificial Sequence
<220> FEATURE:
<223> OTHER INFORMATION: Synthetic Construct

<400> SEQUENCE: 33
gggggtctaa gagcttgtaa aaag					24

<210> SEQ ID NO 34
<211> LENGTH: 29
<212> TYPE: DNA
<213> ORGANISM: Artificial Sequence
<220> FEATURE:
<223> OTHER INFORMATION: Synthetic Construct

<400> SEQUENCE: 34
gtttgtgtgt gcatctgtaa gcatgtatc					29

<210> SEQ ID NO 35

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
gatcccaagc tcttcctctt                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct

<400> SEQUENCE: 36
acgtttgtgt gtgcatctgt                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct

<400> SEQUENCE: 37
caaacccgac taccagcaac                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic Construct

<400> SEQUENCE: 38
gagccatgtt catgccactg                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
ttcttgagcc cagaaggtta                                              20

<210> SEQ ID NO 40
<211> LENGTH: 27
<212> TYPE: DNA
<213> ORGANISM: Artificial Sequence
<220> FEATURE:
<223> OTHER INFORMATION: Synthetic Construct

<400> SEQUENCE: 40
attctaccag caacaacaca aataaac                                      27

<210> SEQ ID NO 41
<211> LENGTH: 18
<212> TYPE: DNA
<213> ORGANISM: Artificial Sequence
<220> FEATURE:
<223> OTHER INFORMATION: Synthetic Construct

<400> SEQUENCE: 41
```
gtgagtcaat tccccaag                                                 18

<210> SEQ ID NO 42
<211> LENGTH: 22
<212> TYPE: DNA
<213> ORGANISM: Artificial Sequence
<220> FEATURE:
<223> OTHER INFORMATION: Synthetic Construct

<400> SEQUENCE: 42
gttgtattag tcaatgttct cc                                            22

<210> SEQ ID NO 43
<211> LENGTH: 22
<212> TYPE: DNA
<213> ORGANISM: Artificial Sequence
<220> FEATURE:
<223> OTHER INFORMATION: Synthetic Construct

<400> SEQUENCE: 43
atatgtgagt caattcccca ag                                            22

<210> SEQ ID NO 44
<211> LENGTH: 22
<212> TYPE: DNA
<213> ORGANISM: Artificial Sequence
<220> FEATURE:
<223> OTHER INFORMATION: Synthetic Construct

<400> SEQUENCE: 44
tgtattagtc aatgttctcc ag                                            22

<210> SEQ ID NO 45
<211> LENGTH: 22
<212> TYPE: DNA
<213> ORGANISM: Artificial Sequence
<220> FEATURE:
<223> OTHER INFORMATION: Synthetic Construct

<400> SEQUENCE: 45
atatgtgagt caattcccca ag                                            22

<210> SEQ ID NO 46
<211> LENGTH: 26
<212> TYPE: DNA
<213> ORGANISM: Artificial Sequence
<220> FEATURE:
<223> OTHER INFORMATION: Synthetic Construct

<400> SEQUENCE: 46
tgtattagtc aatgttctcc agagac                                        26

<210> SEQ ID NO 47
<211> LENGTH: 23
<212> TYPE: DNA
<213> ORGANISM: Artificial Sequence
<220> FEATURE:
<223> OTHER INFORMATION: Synthetic Construct

<400> SEQUENCE: 47
cagtggattt ggaaacagaa atg                                           23

<210> SEQ ID NO 48
<211> LENGTH: 23
<212> TYPE: DNA

<213> ORGANISM: Artificial Sequence
<220> FEATURE:
<223> OTHER INFORMATION: Synthetic Construct

<400> SEQUENCE: 48
tcagtaagtt aaaggattgc agg    23

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
cctgggcaac agaataagat    20

<210> SEQ ID NO 50
<211> LENGTH: 22
<212> TYPE: DNA
<213> ORGANISM: Artificial Sequence
<220> FEATURE:
<223> OTHER INFORMATION: Synthetic Construct

<400> SEQUENCE: 50
taggttttta aggaacaggt gg    22

<210> SEQ ID NO 51
<211> LENGTH: 21
<212> TYPE: DNA
<213> ORGANISM: Artificial Sequence
<220> FEATURE:
<223> OTHER INFORMATION: Synthetic Construct

<400> SEQUENCE: 51
acctcatcct gggcaccctg g    21

<210> SEQ ID NO 52
<211> LENGTH: 21
<212> TYPE: DNA
<213> ORGANISM: Artificial Sequence
<220> FEATURE:
<223> OTHER INFORMATION: Synthetic Construct

<400> SEQUENCE: 52
aggcttgagg ccaaccatca g    21

<210> SEQ ID NO 53
<211> LENGTH: 23
<212> TYPE: DNA
<213> ORGANISM: Artificial Sequence
<220> FEATURE:
<223> OTHER INFORMATION: Synthetic Construct

<400> SEQUENCE: 53
acctcatcct gggcaccctg gtt    23

<210> SEQ ID NO 54
<211> LENGTH: 21
<212> TYPE: DNA
<213> ORGANISM: Artificial Sequence
<220> FEATURE:
<223> OTHER INFORMATION: Synthetic Construct

<400> SEQUENCE: 54
aggcttgagg ccaaccatca g    21

<210> SEQ ID NO 55
<211> LENGTH: 70
<212> TYPE: DNA
<213> ORGANISM: Artificial Sequence
<220> FEATURE:
<223> OTHER INFORMATION: Synthetic Construct

<400> SEQUENCE: 55
gtttattgcc caaacattca ttcattcatt cattcagtga gggttcccta agtgcctgtt    60
ctgtgccagt                                                           70

<210> SEQ ID NO 56
<211> LENGTH: 86
<212> TYPE: DNA
<213> ORGANISM: Artificial Sequence
<220> FEATURE:
<223> OTHER INFORMATION: Synthetic Construct

<400> SEQUENCE: 56
gtttattgcc caaacattca ttcattcatt cattcattca ttcattcatt cagtgagggt    60
tccctaagtg cctgttctgt gccagt                                         86

<210> SEQ ID NO 57
<211> LENGTH: 36
<212> TYPE: DNA
<213> ORGANISM: Artificial Sequence
<220> FEATURE:
<223> OTHER INFORMATION: Synthetic Construct

<400> SEQUENCE: 57
actggcacag aacaggcact tagggaaccc tcactg                              36

<210> SEQ ID NO 58
<211> LENGTH: 61
<212> TYPE: DNA
<213> ORGANISM: Artificial Sequence
<220> FEATURE:
<223> OTHER INFORMATION: Synthetic Construct

<400> SEQUENCE: 58
tgtctgtcta tctatctatc tatccatcta tccatccatc ctatgtattt atcatctgtc    60
c                                                                    61

<210> SEQ ID NO 59
<211> LENGTH: 85
<212> TYPE: DNA
<213> ORGANISM: Artificial Sequence
<220> FEATURE:
<223> OTHER INFORMATION: Synthetic Construct

<400> SEQUENCE: 59
tgtctgtcta tctatctatc tatctatcta tctatctatc tatctatcca tctatccatc    60
catcctatgt atttatcatc tgtcc                                          85

<210> SEQ ID NO 60
<211> LENGTH: 30
<212> TYPE: DNA
<213> ORGANISM: Artificial Sequence
<220> FEATURE:
<223> OTHER INFORMATION: Synthetic Construct

<400> SEQUENCE: 60

```
ggacagatga taaatacata ggatggatgg                                          30

<210> SEQ ID NO 61
<211> LENGTH: 13
<212> TYPE: DNA
<213> ORGANISM: Artificial Sequence
<220> FEATURE:
<223> OTHER INFORMATION: Synthetic Construct

<400> SEQUENCE: 61
agatgtttct caa                                                            13

<210> SEQ ID NO 62
<211> LENGTH: 19
<212> TYPE: DNA
<213> ORGANISM: Artificial Sequence
<220> FEATURE:
<223> OTHER INFORMATION: Synthetic Construct

<400> SEQUENCE: 62
aaataaagtg gtttctcaa                                                      19
```

METHODS FOR DETERMINING SEQUENCE PROFILES

CROSS REFERENCE TO RELATED APPLICATION

This application claims priority to U.S. Provisional Application No. 62/256,461, filed Nov. 17, 2015, which is incorporated by reference herein in its entirety.

BACKGROUND

Analysis of short tandem repeats (STRs) of individual human genomes is routinely used, e.g., in human identity testing, and in testing of other organisms. STRs are simple sequence motifs of a few up to several dozen repeat units. Thousands of STRs can be found in the human genome. Since STRs are polymorphic with respect to their number of repeat units, individuals such as human individuals can be distinguished from each other by the unique number of repeat units per allele and per STR region or locus. Therefore, the analysis of STRs is especially useful for identifying human individuals, e.g., in forensic science or parental testing.

The United States Federal Bureau of Investigation (FBI) has established and maintains a Combined DNA Index System (CODIS), a database of STR typing information. Local, state, and national law enforcement agencies use the CODIS system to match forensic DNA evidence collected at crime scenes with STR information in the database. CODIS and other international database systems such as the European Standard Set have proven to be an effective tool for use in solving crimes and identifying individuals.

Generally, analysis of STR regions involves the isolation of genomic DNA of a human individual, followed by a polymerase chain reaction (PCR) amplification step to enrich the nucleic acid sequence containing the target STR regions. After the amplification step of selected genomic fragments, the length of each amplified STR allele is determined using, e.g., capillary electrophoresis, and compared to a standardized allelic ladder. Other methods for determining the length of each amplified STR include hybridization techniques and in some cases, capture and/or reporter probes. Additional techniques for identifying the target STR allele(s) include kinetic measurements of the amplified STR, e.g., melting temperature analysis or mass measurements, e.g., mass spectrometry such as time-of-flight mass spectrometry (MALDI-TOF-MS).

The alleles at a single STR locus may be the same for two different individuals in a population, especially if the individuals are genetically related. The probability that the alleles of two individuals will be identical at several different STR loci decreases as the number of examined loci increases. If a sufficient number of loci are examined, an overall STR allelic pattern that is unique of each individual emerges. Therefore, it is possible to establish with scientific certainty whether or not a DNA sample has originated from a particular individual. As such, an individual's unique pattern of STR alleles can be used as a DNA fingerprint.

BRIEF SUMMARY

The present disclosure provides a method of determining occurrence of a preselected signature in a nucleic acid. The method can include steps of: (a) incorporating a subset of nucleic acid base types into a primed nucleic acid to form an extended nucleic acid, under conditions wherein incorporation of each of the individual nucleic acid base types is not distinguished among the subset of nucleic acid base types; (b) detecting a ternary complex comprising the extended nucleic acid, a polymerase and a preselected nucleic acid base type, wherein the preselected base type is not covalently bound to the extended nucleic acid during the detecting, and wherein the preselected nucleic acid base type is different from the nucleic acid base types in the subset; (c) repeating steps (a) and (b) at least one time; and (d) determining the number of times the preselected nucleic acid base type is detected and the number of times step (b) is carried out to determine the occurrence of the preselected signature.

Also provided is a method of distinguishing target sequences. The method can include steps of: (a) providing a primed nucleic acid that includes a primer hybridized to a template strand, wherein the template strand has a candidate sequence selected from at least two known target sequences; (b) contacting the primed nucleic acid with a polymerase and a subset of nucleic acid base types, whereby the subset of nucleic acid base types incorporates into the primer to produce an extended primed nucleic acid; (c) contacting, under ternary complex stabilizing conditions that preclude incorporation, the extended primed nucleic acid with a polymerase and a preselected nucleic acid base type different from the subset of nucleic acid base types, whereby a ternary complex forms if the preselected nucleic acid base type is the next correct nucleotide for the extended primed nucleic acid product; (d) acquiring a signal produced by the ternary complex; and (e) repeating (b) through (d) at least one time to obtain a series of signals, wherein the series of signals provides a signature that identifies the candidate sequence. Optionally, the series of signals identifies the candidate sequence as one of the at least two known target sequences.

The present disclosure provides a method of determining the presence of a repeat unit within a nucleic acid region in a sample. The method can include steps of: (a) providing a primed nucleic acid that includes a primer hybridized to a template strand with at least one repeat unit downstream of the primer; (b) contacting the primed nucleic acid with a polymerase and a subset of nucleic acid base types, whereby the subset of nucleic acid base types incorporates into the primer to produce an extended primed nucleic acid; (c) contacting, under ternary complex stabilizing conditions that preclude incorporation, the extended primed nucleic acid with a polymerase and a preselected nucleic acid base type different from the subset of nucleic acid base types, whereby a ternary complex forms if the preselected nucleic acid base type is the next correct nucleotide for the extended primed nucleic acid product; and (d) detecting the ternary complex, thereby determining the presence of the repeat unit within the nucleic acid region.

This disclosure further provides a method of determining the number of repeats (repeat units) of a short tandem repeat (STR) region (or other repeat region) in a sample such as a nucleic acid sample. The method includes: contacting a STR product comprising a template strand to be sequenced with a capture primer complementary to the template strand, incorporating a subset of nucleic acid base types into a complementary strand opposite the template strand by extending the capture primer, incorporating a preselected nucleic acid base type that is different than the subset of nucleic base types into the complementary strand, and detecting the presence of the preselected nucleic acid base type in the complementary strand, thereby determining the number of STR repeat units in the STR region.

Other objects, features, and advantages will be apparent to one of skill in the art from the following detailed description and figures.

BRIEF DESCRIPTION OF THE DRAWINGS

FIG. 1A provides a table of 13 CODIS core STR loci and the repeat unit of each allele, and the approximate range for the number of repeats. FIG. 1B shows the chromosomal location of the 13 CODIS core STR regions.

FIG. 2A shows peaks that indicate that a "G" is detected in the TPOX STR. The trace for TPOX-5 shows 6 peaks which is expected. There are 5 peaks from the 5 TPOX-5 STR and a sixth "G" peak that corresponds to the "GGG" sequence in the flanking region.

FIG. 5A shows 2 peaks for the female (XX chromosome) sample and 3 peaks for the male (XY chromosome) sample. The first peak indicates that a "T" in the flanking region outside of the amelogenin region and the last peak represents the "TTT" flanking the amelogenin loci. FIG. 5C is a schematic showing the sequences for an X allele (SEQ ID NO:61) and Y allele (SEQ ID NO:62) of a locus in the amelogenin gene. The sequences are aligned and the positions are arbitrarily numbered to identify the deletion in the X allele compared to the insertion in the Y allele.

DETAILED DESCRIPTION

Figures 1A, 1B:
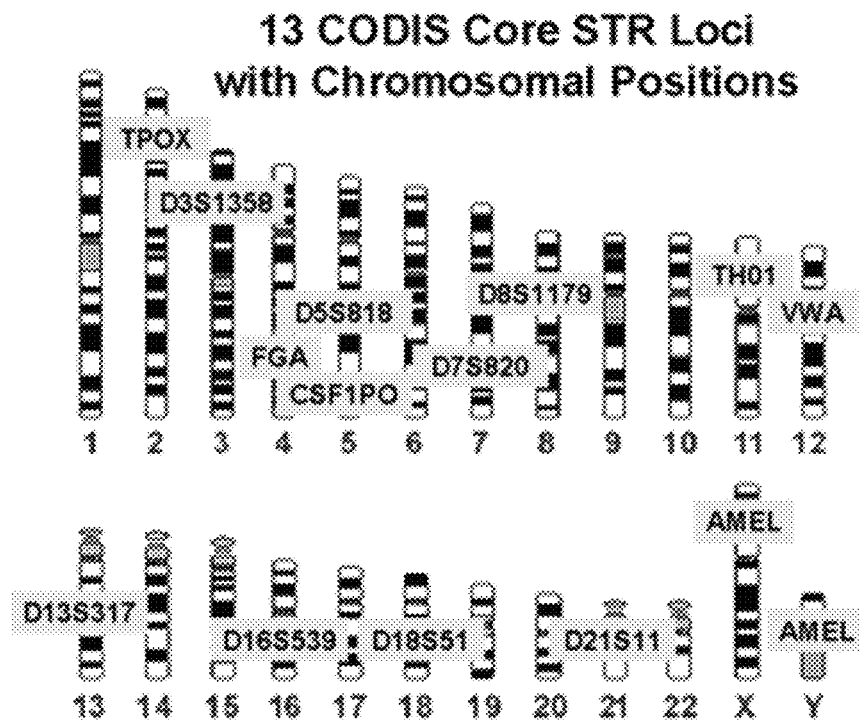
FIG. 1A and FIG. 1B provide the 13 CODIS core STR loci or regions.

The methods provided herein can be used for identifying sequence signatures such as signatures that identify a short tandem repeat (STR) or microsatellite at a target STR or microsatellite region in a nucleic acid sample from an individual. Other types of regions, whether having repeat units or not, can also be identified using the methods set forth herein. The methods are based, in part, on the discovery that the STR allele or microsatellite can be directly determined by way of sequencing with a minimum of examination steps. Also, the method is not biased by the flanking regions that surround the target STR or microsatellite region.

In particular embodiments, the present disclosure provides a method for determining the number of repeats (repeat units) of a short tandem repeat (STR) region in a sample such as a nucleic acid sample. The method includes: contacting a STR product comprising a template strand to be sequenced with a capture primer complementary to the template strand, incorporating a subset of nucleic acid base types into a complementary strand opposite the template strand by extending the capture primer, incorporating a preselected nucleic acid base type that is different than the subset of nucleic base types into the complementary strand, and detecting the presence of the preselected nucleic acid base type in the complementary strand, thereby determining the number of STR repeat units in the STR region. Optionally, the initial step of the method can include amplifying nucleic acids in the sample with a composition comprising a primer pair specific for the STR region to produce the STR product comprising one or more STR repeat units. The template strand can be a sense strand or an antisense strand that contains the STR region.

The practice of the present methods may employ general methods and techniques in the field of organic chemistry, molecular biology, cell biology, and biochemistry including oligonucleotide synthesis, hybridization, denaturation reaction, amplification reaction, extension reaction, detection of hybridization using a label, and sequencing. Such general methods and techniques can be found in standard laboratory manuals such as *Genome Analysis: A Laboratory Manual Series (Vols. I-IV)*. New York: Cold Spring Harbor Press, 1989; Dieffenbach, C W and Dveksler, G S. *PCR Primer: A Laboratory Manual*. New York: Cold Spring Harbor Press, 2003; Lehninger, *Principles of Biochemistry* 6th Ed., New York: W.H. Freeman, 2012; Berg et al. *Biochemistry,* 5th Ed., New York: W. H. Freeman, 2002; Sambrook, *Molecular Cloning: A Laboratory Manual*. New York: Cold Spring Harbor Press, 1989; Ausubel et al., eds., *Current Protocols in Molecular Biology*. New York: John Wiley & Sons, 1994, and Mount, *Bioinformatics: Sequence and Genome Analysis* $2^{nd}$ Ed., New York: Cold Spring Harbor Press, 2004, all of which are herein incorporated in their entirety by reference for all purposes.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "repeat unit," when used in reference to a nucleic acid sequence, refers to a portion of the sequence that is heteropolymeric and that occurs two or more times in the sequence. Typically, repeat units are juxtaposed but in some cases one or more nucleotides can intervene the repeat units. A repeat unit can be, for example, at most 100, 50, 25, 20, 15, 14, 12, 10, 9, 8, 7, 6, 5, 4, 3, or 2 nucleotides in length. Alternatively, or additionally, a repeat unit can be at least, 2, 3, 4, 5, 6, 7, 8, 9, 10, 12, 14, 15, 20, 25, 50 or 100 nucleotides in length.

The term "short tandem repeat (STR) loci" or "short tandem repeat (STR) region" refers to a region of a genome which contains short, repetitive sequence elements, typically, of 2 to 7 base pairs in length. Each sequence element is repeated at least once within an STR and is referred to herein as a "repeat unit" or "repeating unit." The term "STR" also encompasses a region of genomic DNA wherein more than a single repeat unit is repeated in tandem or with intervening bases, provided that at least one of the sequences is repeated at least two times in tandem. For clarity, a sequence such as an STR that is present two times is referred to as being "repeated" two times, a sequence such as an STR that is present three times is referred to as being "repeated" three times etc. Examples of STRs include but are not limited to, a triplet repeat, e.g., [ATC] in tandem; a 4-peat (tetra-repeat), e.g., [GATA] in tandem; and a 5-peat (penta-repeat), e.g., [ATTGC] in tandem and the like. Information about specific STRs that can be used as genetic markers can be found in, for example, the STRbase at the following websites at cstl.nist.gov/strbase and strbase.org. The terms for the particular STR loci as used herein refer to the names assigned to these loci as they are known in the art.

The term "locus," when used in reference to a nucleic acid, refers to the position in the nucleic acid where a nucleotide, nucleic acid sequence or other genetic feature occurs. The term "allele," when used in reference to a genetic locus, refers to any of the alternative nucleotides, sequences or other genetic features that occur at the genetic locus. Exemplary alleles include, but are not limited to single nucleotide polymorphisms (SNPs), insertions and/or deletions (indels), or repeats that occur at a locus. The term "STR allele" refers to an alternative form of the same STR locus, such as a difference in repeat numbers. By way of example, the STR locus D10S1248 may contains between 8 and 19 repeats of the nucleotide sequence [GGAA]. The nucleotide sequence with eight repeats can be represented as $[GGAA]_8$, while the nucleotide sequence of nineteen repeats can be represented as $[GGAA]_{19}$. Each of the different number of repeats represents a different D10S1248 allele. A given STR locus may be heterozygous, meaning that the two alleles (one inherited from each biological parent) are of different lengths and base pair composition, or may be homozygous, meaning that both alleles are of identical length (and usually, but not always, identical base pair composition). Occasionally, an individual's alleles at a given STR locus may differ from the individual's parents due to one or more mutations.

The term "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form including, for example, analogs thereof. Examples of isolated nucleic acid molecules include, but are not limited to, mRNA, siRNA, miRNA, shRNA, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

The term "nucleic acid sequence" or "nucleotide sequence" refers to a nucleic acid material itself and is not restricted to the sequence information (i.e., the succession of letters chosen among the five base letters A, C, G, T, or U) that biochemically characterizes a specific nucleic acid, for example, a DNA or RNA molecule. Nucleic acids shown herein are presented in a 5'-3' orientation unless otherwise indicated.

The terms "polynucleotide," "oligonucleotide" and "nucleic acid" are used interchangeably herein and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Unless denoted otherwise, whenever a polynucleotide sequence is represented, it will be understood that the nucleotides are in 5' to 3' order from left to right and that "A" denotes deoxyadenosine or an adenine base type, "C" denotes deoxycytosine or a cytosine base type, "G" denotes deoxyguanosine or a guanine base type, "T" denotes thymidine or a thymine base type, and "U" denotes deoxyuridine or a uracil base type, unless otherwise noted. The letters A, C, G, and T can be used to refer to the bases themselves, to nucleosides, or to nucleotides comprising the bases, as is standard in the art. In naturally-occurring polynucleotides, the inter-nucleoside linkage is typically a phosphodiester bond, and the subunits are referred to as nucleotides.

The term "type" is used to identify molecules that share the same chemical structure. For example, a method set forth herein can employ a first cytosine nucleotide in a first step and a second cytosine nucleotide in a second step. The cytosine nucleotides used in those steps will be understood to be the same type as each other. Similarly, two polymerase molecules that have the same structure are the same type of polymerase even if used for different functions. The term "nucleic acid base type" refer to a nucleobase (i.e., a nitrogenous base, a five-carbon sugar (ribose or deoxyribose), and at least one phosphate group), an analog thereof, or a derivative thereof that can be incorporated into a strand of DNA or RNA. A nucleic acid base type includes a ribonucleotide, deoxyribonucleotide, nucleoside, modified nucleotide, or any monomer component that comprises the template nucleic acid or the nucleic acid being synthesized as part of the sequencing process. Optionally, the 3' OH group of the nucleotide is modified with a moiety. The moiety may be a 3' reversible or irreversible terminator. A nucleotide may be adenine, cytosine, guanine, thymine, or uracil. Optionally, a nucleotide has an inosine, xanthanine, hypoxanthanine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP and ddCTP). The sequential order of nucleic acid base types or nucleobases of a single stranded DNA or RNA molecule is used to define the nucleic acid sequence of the molecule.

The term "polymerase chain reaction" or "PCR" refers to an amplification of a nucleic acid (nucleotide sequence) consisting of an initial denaturation step which separates the strands of a double-stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, *The Polymerase Chain Reaction*, Boston: BirkHauser, 1994). Each of the above steps may be conducted at a different temperature, preferably using an automated thermocycler or similar device. If desired, RNA samples can be converted to DNA/RNA heteroduplexes or to duplex cDNA by methods known to one of skill in the art. The PCR method also includes reverse transcriptase-PCR and other reactions that follow principles of PCR.

The term "primer" refers to a polynucleotide (oligonucleotide) and analogs thereof that are capable of selectively annealing or hybridizing to a target nucleic acid including but not limited to a SNP, a STR or mutation region, or a "template", a target region flanking sequence or to a corresponding primer-binding site of an amplification product. A primer serves as an initiation primer for DNA synthesis under suitable conditions, such as in the presence of appropriate enzyme(s), cofactors, substrates, e.g., nucleotides (dNTPs) and the like. A primer allows the synthesis of a sequence complementary to the corresponding polynucleotide template, flanking sequence or amplification product from the primer's 3' end. Typically a primer can be between about 10 to 100 nucleotides in length. A primer can be a first nucleic acid molecule that is physically separable from a template nucleic acid molecule following dehybridization. Alternatively, a primer can be a primer region of a nucleic acid molecule that hybridizes to a template region of the nucleic acid molecule such that the primer region is not physically separable from the template region upon mere dehybridization. For example, a primer can be covalently attached to a template via a hairpin or stem-loop structure.

Typically, a PCR reaction employs an "amplification primer pair" also referred to as an "oligonucleotide primer pair" including an "upstream" or "forward" primer and a "downstream" or "reverse" primer, which delimit a region of the RNA or DNA to be amplified. A first primer and a second primer may be either a forward or reverse primer respectively, and are used interchangeably herein and are not to be limiting.

The term "amplifying" refers to a process whereby at least a portion of a nucleotide sequence is replicated using, for example, any of a broad range of primer extension reactions. Exemplary primer extension reactions include, but are not limited to, polymerase chain reaction (PCR), rolling circle amplification (RCA), multiple displacement amplification (MDA), and random primer amplification. Unless specifically stated, "amplifying" refers to a single replication or to an arithmetic, logarithmic, or exponential amplification.

The terms "amplicon," "amplification product," and "amplified sequence" are used interchangeably herein and refer to a broad range of nucleic acids produced by techniques for increasing nucleotide sequences, either linearly or exponentially. An amplicon can be double-stranded or single-stranded, and can include the separated component strands obtained by denaturing a double-stranded amplification product. For example, the amplicon of one amplification cycle can serve as a template in a subsequent amplification cycle. Exemplary amplification techniques include, but are not limited to, PCR or any other method employing a primer extension step. Amplification methods can comprise thermal-cycling or can be performed isothermally. The terms "amplification product" and "amplified sequence" may include products from any number of cycles of amplification reactions, whether the products are copies or complements of the template that was amplified.

The term "extension" can refer to the amplification cycle after the oligonucleotide primer and target nucleic acid have annealed to one another, wherein the polymerase enzyme catalyzes primer extension, thereby enabling amplification, using the target nucleic acid as a replication template. In some embodiments, "extension" can refer to a process of adding at least one nucleotide to a nucleic acid in a non-amplification process. A nucleotide that is added to a nucleic acid by extension is said to be incorporated into the nucleic acid. Accordingly, the term "incorporating" can be used to refer to the process of joining a nucleotide to the 3' end of a primer by formation of a phosphodiester bond.

The term "sample" refers to a sample suspected of containing a nucleic acid and can comprise a cell, chromosomes isolated from a cell (e.g., a spread of metaphase chromosomes), genomic DNA, RNA, cDNA and the like. Samples can be of human, non-human, animal, vertebrate, mammalian, fish, invertebrate, plant, prokaryotic, eukaryotic, microbial, viral, or synthetic origins encompassing any organism containing nucleic acid, including, but not limited to, cloned, synthetic constructs, bacteria, viruses, microbes, plants, livestock, household pets, and human samples. Accordingly, the term "nucleic acid sample" may refer to nucleic acid found in, or obtained from, biological sources including, but not limited to, for example, hair; stool; blood; plasma; serum; tissue; urine; saliva; cheek cells; vaginal cells; skin for example skin cells contained in fingerprints; bone; tooth; buccal sample; amniotic fluid containing placental cells; amniotic fluid containing fetal cells; and semen. It is contemplated that samples may be collected invasively or noninvasively. In addition from originating from a biological source, a nucleic acid sample can be on, in, within, from or found in conjunction with for example, but not limited by a fiber, fabric, cigarette, chewing gum, adhesive material, soil, inanimate objects and other forensic samples.

The term "nucleic acid sample" refers to nucleic acid found in a biological source, for example. A nucleic acid sample can also be outside of a biological source, for example, having been derived from the biological source. In particular embodiments, a biological sample can be obtained from a synthetic source or other non-biological source.

The term "sequencing run" refers to a repetitive process of physical or chemical steps that is carried out to obtain signals indicative of a sequence of nucleotides in a nucleic acid. The process can be carried out until signals from the process can no longer distinguish nucleotides of the target with a desired level of certainty. In some embodiments, completion can occur earlier, for example, once a desired amount of sequence information has been obtained, once a preselected signature has been observed, or once a preselected signature has been repeatedly observed a preselected number of times. In some embodiments, a sequencing run is terminated when signals are no longer obtained from one or more target nucleic acid molecules from which signal acquisition was initiated.

The terms "cycle" or "round," when used in reference to a sequencing run, refer to the portion of a sequencing run that is repeated to indicate the presence of a nucleotide or sequence signature in a nucleic acid. Typically, a cycle or round includes several steps such as steps for delivery of reagents, washing away unreacted reagents and detection of signals indicative of changes occurring in response to added reagents.

The term "signature," when used in reference to a nucleic acid, refers to information that signifies the order and type for at least a subset of nucleotide types in the nucleic acid. The information can be at single nucleotide resolution or at low resolution. A series of "A," "T," "G," and "C" letters is a well known sequence representation for DNA that can be correlated, at single nucleotide resolution, with the actual sequence of a DNA molecule.

The term "low resolution," when used in reference to a sequence representation refers to a resolution at which at least one type of nucleotide in a nucleic acid can be distinguished from at least a first other type of nucleotide in the nucleic acid, but cannot necessarily be distinguished from a second other type of nucleotide in the nucleic acid. For example, low resolution can mean that two or three of four possible nucleotide types can be indicated as candidates for residency at a particular position in the sequence while the two or three nucleotide types cannot necessarily being distinguished from each other in the sequence representation.

The term "degenerate" refers to ambiguity regarding the identification of two or more different states. When used in reference to a position in a nucleic acid representation, the term refers to a position which two or more nucleotide types are identified as candidate occupants in the corresponding position of the actual nucleic acid sequence. A degenerate position in a nucleic acid can have, for example, 2, 3 or 4 nucleotide types as candidate occupants. In particular embodiments, the number of different nucleotide types at a degenerate position in a sequence representation can be at least two and no more than two. In other embodiments, the number of different nucleotide types at a degenerate position in a sequence representation can be at least two and no more than three. In other embodiments, the number of different nucleotide types at a degenerate position in a sequence representation can be at least two and no more than four. In other embodiments, the number of different nucleotide types at a degenerate position in a sequence representation can be at least three and no more than three. In other embodiments, the number of different nucleotide types at a degenerate position in a sequence representation can be at least three and no more than four. In other embodiments, the number of different nucleotide types at a degenerate position in a sequence representation can be at least four and no more than four. Typically, the number of different nucleotide types at a degenerate position in a sequence representation can be less than the number of different nucleotide types present in the actual nucleic acid sequence that is represented.

The term "sequencing-by-binding" refers to a sequencing technique wherein specific binding of a polymerase to a primed template nucleic acid is used for identifying the next correct nucleotide to be incorporated into the primer strand of the primed template nucleic acid. The specific binding interaction can optionally precede chemical incorporation of the nucleotide into the primer strand, and so identification of the next correct nucleotide can take place without incorporation of the next correct nucleotide.

The term "ternary complex" refers to an intermolecular association between a polymerase, a primed nucleic acid and a nucleotide. Typically, the polymerase facilitates interaction between the nucleotide and a template strand of the primed nucleic acid. A cognate nucleotide can interact with the template strand via Watson-Crick hydrogen bonding.

The term "stabilize" means to hold steady or limit fluctuations. "Stabilizing" a ternary complex refers to promoting or prolonging the existence of the ternary complex or inhibiting disruption of the ternary complex. Generally, stabilization of the ternary complex prevents incorporation of the nucleotide component of the ternary complex into the primed nucleic acid component of the ternary complex.

The term "next correct nucleotide" refers to the nucleotide type that will incorporate at the 3' end of a primer to complement a base in a template strand to which the primer is hybridized. The base in the template strand is referred to as the "next template nucleotide" and is immediately 5' of the base in the template that is hybridized to the 3' end of the primer. The next correct nucleotide can be referred to as the cognate of the next template nucleotide and vice versa. A nucleotide having a base that is not complementary to the next template base is referred to as an "incorrect" (or "non-cognate") nucleotide.

The term "polymerase" can be used to refer to a protein that forms a ternary complex with a primed nucleic acid and a cognate nucleotide. Exemplary polymerases include, but are not limited to, DNA polymerase, RNA polymerase, reverse transcriptase, primase and transferase. Typically, the polymerase includes one or more active sites at which nucleotide binding and/or catalysis of nucleotide polymerization may occur. The polymerase may catalyze the polymerization of a cognate nucleotide to the 3'-end of a primer bound to its complementary nucleic acid strand. For example, a polymerase catalyzes the addition of a next correct nucleotide to the 3'-OH group of the primer via a phosphodiester bond, thereby chemically incorporating the nucleotide into the primer. Optionally, the polymerase used in the provided methods is a processive polymerase. Optionally, the polymerase used in the provided methods is a distributive polymerase. Optionally, a polymerase may be inhibited from catalyzing the polymerization of a cognate nucleotide to the 3'-end of a primer bound to its complementary nucleic acid strand.

As used herein, the above terms have the meanings ascribed to them unless specified otherwise.

The present disclosure provides a method of determining occurrence of a preselected signature in a nucleic acid. The method can include steps of: (a) incorporating a subset of nucleic acid base types into a primed nucleic acid to form an extended nucleic acid, under conditions wherein incorporation of each of the individual nucleic acid base types is not distinguished among the subset of nucleic acid base types; (b) detecting a ternary complex comprising the extended nucleic acid, a polymerase and a preselected nucleic acid base type, wherein the preselected base type is not covalently bound to the extended nucleic acid during the detecting, and wherein the preselected nucleic acid base type is different from the nucleic acid base types in the subset; (c) repeating steps (a) and (b) at least one time; and (d) determining the number of times the preselected nucleic acid base type is detected and the number of times step (b) is carried out to determine the occurrence of the preselected signature. Preselected signatures that can be identified using the provided methods include, but are not limited to, polymorphisms (SNPs), insertions and/or deletions (indels), repeat units, fusions, copy number variants or other regions of interest.

In particular embodiments, the method can include a step of separating the preselected nucleic acid base type from the primed nucleic acid prior to step (c). This can be useful, for example, when the preselected nucleic acid base type is not capable of being incorporated into the primed nucleic acid or when it is present in conditions that inhibit its incorporation. Optionally, the above method can include a step of separating the subset of nucleic acid base types from the primed nucleic acid prior to step (b). Separation of nucleotides from one or more other reaction components can be carried out by any of a variety of steps including, but not limited to wash methods such as those set forth below, liquid-liquid extraction, solid-phase extraction, chromatographic techniques or the like.

Alternatively or additionally to the above optional steps, a step of incorporating the preselected nucleic acid base type into the primed nucleic acid prior to step (c) can be carried out. Such a step is useful for allowing further cycles of the sequencing reaction to proceed. Techniques and conditions for incorporation of nucleotides are set forth in further detail below and in U.S. Ser. No. 14/805,381, which is incorporated herein by reference in its entirety.

Also provided is a method of distinguishing target sequences. The method can include the steps of: (a) providing a primed nucleic acid that includes a primer hybridized to a template strand, wherein the template strand has a candidate sequence selected from at least two known target sequences; (b) contacting the primed nucleic acid with a polymerase and a subset of nucleic acid base types, whereby the subset of nucleic acid base types incorporates into the primer to produce an extended primed nucleic acid; (c) contacting, under ternary complex stabilizing conditions that preclude incorporation, the extended primed nucleic acid with a polymerase and a preselected nucleic acid base type different from the subset of nucleic acid base types, whereby a ternary complex forms if the preselected nucleic acid base type is the next correct nucleotide for the extended primed nucleic acid product; (d) acquiring a signal produced by the ternary complex; and (e) repeating (b) through (d) at least one time to obtain a series of signals, wherein the series of signals provides a signature that identifies the candidate sequence. Optionally, the series of signals identifies the candidate sequence as one of the at least two known target sequences. Optionally, the method can further include a step of separating the subset of nucleic acid base types from the primed nucleic acid prior to step (c). In particular embodiments, the method can include a step of separating the preselected nucleic acid base type from the primed nucleic acid between step (b) and step (c). As a further option, a step of incorporating the preselected nucleic acid base type into the primed nucleic acid after step (d) can be carried out.

The methods set forth herein can be applied to any of a variety of target sequences. For example, the target sequence can be a locus having two or more alleles, such that individual alleles are treated as candidate alleles. An exemplary locus is a single nucleotide polymorphism (SNP) site having two or more alleles. In such embodiments, one of the nucleotide alleles is identical to or complementary to the preselected nucleic acid base type that is used in a method herein. In some embodiments the locus is an indel and an inserted allele of the indel can include at least one nucleic acid base type that is identical to or complementary to the preselected nucleic acid base type used in a method herein. As set forth in further detail below, the target sequence can be a repeat region having two or more repeat units (e.g. an STR region).

Target sequences evaluated in a method set forth herein can be different loci of a single genome. As such the methods can be used to identify genetic regions of interest within an individual's genome. The target sequences can be from different individuals of the same species. In this case, the methods can be used to identify, distinguish or characterize individuals. For example, the methods can be used in a diagnostic or forensic capacity. The target sequences can be from different species of organism. As such, the methods can be used to identify, distinguish or characterize types of organisms. For example, the methods can be used to detect pathogens or diagnose individuals suspected of being infected with a pathogen, or the methods can be used for metagenomic analysis such as evaluation of the flora of the human digestive system.

The methods of distinguishing target sequences set forth herein can be used to identify a target sequence based on comparison to a known reference sequence. However, two target sequences can be distinguished absent a reference sequence by performing the methods using two different candidate nucleic acids and comparing the signatures obtained for each.

Accordingly, this disclosure also provides a method of distinguishing target sequences that includes the steps of: (a) providing a primed nucleic acid that includes a primer hybridized to a template strand, wherein the template strand has a candidate sequence selected from at least two known target sequences; (b) contacting the primed nucleic acid with a polymerase and a subset of nucleic acid base types, whereby the subset of nucleic acid base types incorporates into the primer to produce an extended primed nucleic acid; (c) contacting, under ternary complex stabilizing conditions that preclude incorporation, the extended primed nucleic acid with a polymerase and a preselected nucleic acid base type different from the subset of nucleic acid base types, whereby a ternary complex forms if the preselected nucleic acid base type is the next correct nucleotide for the extended primed nucleic acid product; (d) acquiring a signal produced by the ternary complex; (e) repeating (b) through (d) at least one time to obtain a series of signals, wherein the series of signals provides a signature that distinguishes the target sequence from another of the at least two known target sequences; and (f) performing (b) through (d) for a second primed nucleic acid that includes a primer hybridized to a second template strand, wherein the template strand has a second candidate sequence selected from the at least two known target sequences, thereby obtaining a second set of signals. Optionally, the method can further include a step (g) comparing the second series of signals to the series of signals acquired in (d), thereby distinguishing the at least two known target sequences.

It will be understood that a signature detected using methods set forth herein can be used to distinguish two or more different sequences from each other. As demonstrated in Example 3, herein below, such signatures can be used to distinguish alleles at a particular locus. Other sequences can be distinguished by appropriate choice of nucleotide mixtures to be used in the examination and extension steps of the methods. For example, the methods can be used to distinguish different genes, different chromosomes, different genomes, different organisms or even different populations of organisms (e.g. metagenomic samples such as those obtained from a human digestive system). Exemplary applications for evaluating sequences based on low resolution signatures are set forth in US Pat. App. Pub. No. 2012/0295262 A1, which is incorporated herein by reference. It will be understood that the methods set forth herein can be used to generate signatures for those and other applications. In particular embodiments, the methods set forth herein can be used for characterizing nucleic acid sequence repeats. The methods can be used advantageously to provide a signature for each repeat unit. The signatures can be counted to determine the number of repeat units present in a repeat region.

This disclosure further provides a method of determining the presence of a repeat unit within a nucleic acid region in a sample. The method can include steps of: (a) providing a primed nucleic acid that includes a primer hybridized to a template strand with at least one repeat unit downstream of the primer; (b) contacting the primed nucleic acid with a polymerase and a subset of nucleic acid base types, whereby the subset of nucleic acid base types incorporates into the primer to produce an extended primed nucleic acid; (c) contacting, under ternary complex stabilizing conditions that preclude incorporation, the extended primed nucleic acid with a polymerase and a preselected nucleic acid base type different from the subset of nucleic acid base types, whereby a ternary complex forms if the preselected nucleic acid base type is the next correct nucleotide for the extended primed nucleic acid product; and (d) detecting the ternary complex, thereby determining the presence of the repeat unit within the nucleic acid region. Optionally, the method can further include a step of separating the subset of nucleic acid base types from the primed nucleic acid prior to step (c). In particular embodiments, the method can include a step of separating the preselected nucleic acid base type from the primed nucleic acid after step (c). As a further option, a step of incorporating the preselected nucleic acid base type into the primed nucleic acid after step (d) can be carried out.

The number of repeat units in a repeat region can be determined by counting the number of times a particular sequence signature is observed. Thus, the number of repeats can be determined from the number of times a ternary complex is observed or detected. Generally, it is advantageous to continue a sequencing run beyond the stage where a known number of repeats is detected. Specifically, appropriate steps of the sequencing run that are used to detect the signature can be carried out until the signature is no longer detected, thereby obtaining confirmation that further repeats are not present in the nucleic acid under investigation. Once this confirmation is obtained the sequencing run can, optionally, be terminated.

Generally, the composition of the subset of nucleic acid base types and the composition of the preselected nucleic acid base type are selected to produce an informative signature sequence from the target sequence(s). For example, these compositions can be selected to produce a unique signature for each repeat unit in a repeat region or to produce a distinguishable signature between alleles at a predefined locus. Some illustrative examples of the compositions that can be used in a method of the present disclosure include, but are not limited to, the subset of nucleic acid base types can be complementary to only one nucleic acid base type in the primed nucleic acid; the subset of nucleic acid base types can be complementary to at least one but no more than three nucleic acid base types in the primed nucleic acid; the subset of nucleic acid base types can be complementary to at least two but no more than three nucleic acid base types in the primed nucleic acid; the subset of nucleic acid base types can be complementary to at least one but no more than two nucleic acid base types in the primed nucleic acid; the subset of nucleic acid base types can be complementary to at least two but no more than two nucleic acid base types in the primed nucleic acid; or the subset of nucleic acid base types can be complementary to at least three but no more than three nucleic acid base types in the primed nucleic acid. Exemplary compositions and the signatures they produce are set forth in the Examples section below.

Optionally, the subset of nucleic acid base types used in a method herein can include only a single nucleic acid base type. The single nucleic acid base type can be a naturally occurring nucleotide that pairs specifically with only one cognate base type in a template strand. Alternatively, the single nucleotide base type can be a promiscuous (aka degenerate) base analog that pairs with two or more cognate base types. For example, inosine can be used under varying conditions to selectively pair with 2, 3 or 4 base types. The analog 8-oxo-G can be useful for selectively pairing with C and A bases in a template strand, but not with other bases in the strand (see, for example, Petrie and Joyce *Nucleic Acids Res.* 38(22): 8095-8104 (2010), which is incorporated herein by reference). The analog 2-Aminopurine can be useful for selectively pairing with C and T bases in a template strand, but not with other bases in the strand (see, for example, Wilhelmsson *Quart. Rev. Biophys.* 43:159-183 (2010), which is incorporated herein by reference).

In particular embodiments, the subset of nucleic acid base types will include only unlabeled nucleic acid base types (i.e. nucleotides that lack any exogenous label moieties). Alternatively, one or more of the nucleotides in the subset can have a label moiety. Multiple nucleotides that are present in a subset can include the same label. Alternatively, nucleotides in the subset can have unique labels allowing them to be distinguished one from the other.

Similarly, a preselected nucleic acid base type that is used in a method set forth herein can be labeled (e.g. with an exogenous label moiety) or unlabeled (e.g. lacking any exogenous label moiety). In some embodiments, different preselected base types can be used. The different base types can be unlabeled, labeled with a common label, or labelled with different labels that distinguish one preselected base type from another. In particular embodiments, the labeled nucleotides do not include any chemical moieties that preclude or inhibit further extension once incorporated. For example, the labeled nucleotides can have 3'-OH moieties. The 3' position thus lacks a terminator moiety such as those typically used in reversible terminator, sequencing by synthesis techniques.

method set forth herein can be repeated using the same subset of nucleic acid base types for multiple rounds of sequencing. The same subset of nucleic acid base types can be used for one, some or all of the repetitions. Alternatively, the composition of the subset of nucleic acid bases can differ between two or more rounds of the sequencing run.

Accordingly, this disclosure provides a method of distinguishing target sequences that includes the steps of: (a) providing a primed nucleic acid that includes a primer hybridized to a template strand, wherein the template strand has a candidate sequence selected from at least two known target sequences; (b) contacting the primed nucleic acid with a polymerase and a subset of nucleic acid base types, whereby the subset of nucleic acid base types incorporates into the primer to produce an extended primed nucleic acid; (c) contacting, under ternary complex stabilizing conditions that preclude incorporation, the extended primed nucleic acid with a polymerase and a preselected nucleic acid base type different from the subset of nucleic acid base types, whereby a ternary complex forms if the preselected nucleic acid base type is the next correct nucleotide for the extended primed nucleic acid product; (d) acquiring a signal produced by the ternary complex; (e) repeating (b) through (d) at least one time to obtain a series of signals, wherein the series of signals provides a signature that identifies the candidate sequence; (f) repeating (b) and (c) at least one time using a second subset of nucleic acid base types instead of the subset of nucleic acid base types, whereby the second subset of nucleic acid base types incorporates into the extended primed nucleic acid to produce a further extended primed nucleic acid, and whereby a second ternary complex forms for the further extended primed nucleic acid product; and (g) acquiring a second signal produced by the second ternary complex, wherein the first and second signals provide a signature that identifies the candidate sequence. Optionally, the first and second signals identifies the candidate sequence as one of the at least two known target sequences.

In some embodiments, the first preselected nucleic acid base type and the second preselected nucleic acid base type are complementary to different nucleic acid base types in the template strand. Alternatively, the first preselected nucleic acid base type and the second preselected nucleic acid base type are complementary to the same nucleic acid base type in the template strand.

As described throughout, the method provided herein can be used for sequencing STR region(s) to determine number of repeat units present each STR region(s). The methods can be used to count or otherwise characterize other nucleic acid repeats as well.

Examples without limitation of STR regions that can be analyzed using the method provided herein include D1S1656, D2S441, D2S1338, D2S1360, D3S1358, D3S1744, D4S2366, D5S818, D5S2500, D6S474, D6S1043, D7S820, D7S1517, D8S1132, D8S1179, D10S1248, D10S2325, D12S391, D13S317, D16S539, D18S51, D19S433, D21S11, D21S2055, D22S1045, CSF1PO, DYS391, F13A01, F13B, FGA, LPL, Penta C, Penta D, Penta E, SE33, TH01, TPOX, VWA, DXS101, DXS6789, DXS6797, DXS6800, DXS6807, DXS6810, DXS7132, DXS7133, DXS7423, DXS7424, DXS8377, DXS8378, DXS981, DXS9895, DXS9898, DXS9902, GATA165B12, GATA172D05, GATA31E08, HPRTB, AMEL, DYS19, DYS385, DYS389-I, DYS389-II, DYS390, DYS392, DYS393, DYS437, DYS438, DYS439, and SPY.

The STR region can be recognized as a CODIS STR locus, European Standard Set (ESS) STR locus, United Kingdom Core STR locus (e.g., SGM Plus or SGM+ region), German Core STR locus, Interpol Standard Set of STR locus, and the like. Examples of a CODIS STR locus include CSF1PO, FGA, TH01, TPOX, VWA, D3S1358, D5S818, D7S820, D8S1179, D13S317, D16S539, D18S51, D21S11, D1S1656, D2S441, D2S1338, D10S1248, D12S391, D19S433, and D22S1045. A detailed description of the current set of CODIS loci can be found in, for example, Hares, D R, Forensic Sci. Int. Genet., 2015, 17:33-34, the disclosure of which is herein incorporated by reference in its entirety for all purposes. Non-limiting examples of a SGM+ locus include FGA, TH01, VWA, D2S1338, D3S1358, D8S1179, D16S539, D18S51, D19S433, and D21S11. A sex determination STR locus that is specific to the X chromosome can be DXS101, DXS6789, DXS6797, DXS6800, DXS6807, DXS6810, DXS7132, DXS7133, DXS7423, DXS7424, DXS8377, DXS8378, DXS981, DXS9895, DXS9898, DXS9902, GATA165B12, GATA172D05, GATA31E08, HPRTB. Non-limiting examples of a sex determination locus that is specific to the Y chromosome include AMEL, DYS19, DYS385, DYS389-I, DYS389-II, DYS390, DYS392, DYS393, DYS437, DYS438, DYS439, and SPY.

The method may include detecting or determining the number of repeat units of one or more selected repeat regions, e.g., 1, 2, 3, 4, 5, 6, 7, 8, 9, 10, 11, 12, 13, 14, 15, 16, 17, 18, 19, 20 or more repeat regions (e.g. STR regions). Thus, the steps of a sequencing technique set forth herein can be repeated at least 1, 2, 3, 4, 5, 6, 7, 8, 9, 10, 11, 12, 13, 14, 15, 16, 17, 18, 19, 20 or more times. Optionally, the selected STR regions are one or more CODIS alleles, one or more STM+ alleles, one or more sex determination alleles, or any combination thereof. Optionally, the selected STR regions are one or more CODIS alleles and one or more sex determination alleles, or any combination thereof. Optionally, the selected STR regions are one or more STM+ loci and one or more sex determination loci, or any combination thereof.

1 STR region, 2 STR regions, 3 STR regions, 3 STR regions, 3 STR regions, 4 STR regions, 5 STR regions, 6 STR regions, 7 STR regions, 8 STR regions, 9 STR regions, 10 STR regions, 11 STR regions, 12 STR regions, 13 STR regions, 14 STR regions, 15 STR regions, 16 STR regions, 17 STR regions, 18 STR regions, 19 STR regions, 20 STR regions or more STR regions that are included in the CODIS STR loci set can be analyzed. Optionally, 1 STR region, 2 STR regions, 3 STR regions, 3 STR regions, 3 STR regions, 4 STR regions, 5 STR regions, 6 STR regions, 7 STR regions, 8 STR regions, 9 STR regions, 10 STR regions, or more STR regions that are included in the SGM+ loci set are analyzed. Optionally, 1 STR region, 2 STR regions, 3 STR regions, 3 STR regions, 3 STR regions, 4 STR regions, 5 STR regions, 6 STR regions, 7 STR regions, 8 STR regions, 9 STR regions, 10 STR regions, 11 STR regions, 12 STR regions, 13 STR regions, 14 STR regions, 15 STR regions, 16 STR regions, 17 STR regions, 18 STR regions, 19 STR regions, 20 STR regions or more STR regions that are included in the sex determination STR loci set are analyzed.

The selected STR regions that are used for amplification and sequencing according to the methods disclosed herein can comprise or consist of CSF1PO, FGA, TH01, TPOX, VWA, D3S1358, D5S818, D7S820, D8S1179, D13S317, D16S539, D18S51, D21S11, D1S1656, D2S441, D2S1338, D10S1248, D12S391, D19S433, D22S1045, and optionally, AMEL Optionally, the selected STR regions comprise or consist of CSF1PO, FGA, TH01, TPOX, VWA, D3S1358, D5S818, D7S802, D8S1179, D13S317, D16S539, D18S51, D21S11, and optionally, AMEL. Optionally, the selected STR regions comprise or consist of FGA, TH01, VWA, D2S1338, D3S1358, D8S1179, D16S539, D18S51, D19S433, D21S11, and optionally, AMEL Optionally, the STR region is a STR repeat unit selected from the group consisting of AAAG, AAAGA, AAGG, TAGG, AATG, AGAT, AGAC, ATT, CTTT, GAAA, GATA, GGAA, TAGA, TCTA, TCAA, TGCC, TTCC, TCTG, or a reverse complement thereof. In some instances, if the STR repeat unit is AGAT, AATG, GATA, or GAAA, the subset of nucleic acid base types are adenine base types and thymine base types and the preselected base type is a guanine base type.

In some cases, the sex determination allele is amelogenin (AMEL). If the presence of the AMEL allele is detected using the method provided herein, the subset of nucleic acid base types are adenine base types and guanine base types and the preselected nucleic acid base type is a thymine base type.

Genomic DNA such as human genomic DNA that contains a signature region, repeat region or STR region can be extracted or isolated from a tissue sample. Non-limiting tissue samples include blood, serum, plasma, semen, urine, saliva, tears, sweat, mucus, vaginal cells, hair, bone, nail, skin, buccal samples, amniotic fluid containing placental cells or fetal cells, other bodily secretions, and any combination thereof. In some cases, the tissue sample is found with a forensic sample.

Genomic DNA can be prepared for use in the methods of the present disclosure using any procedure of sample preparation that is compatible with the subsequent amplification of DNA. Such procedures are known by those skilled in the art. Some exemplary techniques include DNA purification by phenol extraction (see, e.g., Sambrook et al., Molecular Cloning: A Laboratory Manual. New York: Cold Spring Harbor Press, 1989), and partial purification by salt precipitation (see, e.g., Miller et al., *Nucl Acids Res,* 1988, 16:1215) or chelex (see, e.g., Walsh et al., *Biotechniques,* 1991, 10:506-513; Comey et al., *J Forensic Sci,* 1994, 39:1254) and the release of unpurified material using untreated blood (see, e.g., Burckhardt, *PCR Methods and Applications,* 1994, 3:239-243; McCabe, *PCR Methods and Applications,* 1991, 1:99-106; Nordvag, *Biotechniques,* 1992, 12(4): 490-492).

Once a nucleic acid sample of DNA is prepared, optionally, the target nucleic acid (e.g. target having an STR locus) can be amplified or a plurality of target loci (e.g. target STR loci) can be co-amplified in a multiplex amplification step. Any of a number of different amplification methods can be used to amplify the loci, such as, for example, PCR, transcription based amplification, rolling circle amplification and strand displacement amplification. Multiplex amplification can be performed via PCR, in which a DNA sample is subjected to amplification using primer pairs specific to each STR loci in the multiplex.

Non-limiting examples of amplification primer sets are provided below.

TABLE 1

Primer Pairs for STR Loci

| STR locus | Primer Pair | SEQ ID NO: |
|---|---|---|
| CSF1PO | 5'-AACCTGAGTCTGCCAAGGACTAGC-3' | 1 |
|  | 5'-TTCCACACACCACTGGCCATCTTC-3' | 2 |
| CSF1PO | 5'-CCGGAGGTAAAGGTGTCTTAAAGT-3' | 3 |
|  | 5'-ATTTCCTGTGTCAGACCCTGTT-3' | 4 |
| FGA | 5'-GGCTGCAGGGCATAACATTA-3' | 5 |
|  | 5'-ATTCTATGACTTTGCGCTTCAGGA-3' | 6 |
| TH01 | 5'-ATTCAAAGGGTATCTGGGCTCTGG-3' | 7 |
|  | 5'-GTGGGCTGAAAAGCTCCCGAT AT-3' | 8 |
| TPOX | 5'-ACTGGCACAGAACAGGCACTTAGG-3' | 9 |
|  | 5'-GGAGGAACTGGGAACCACACAGGTTA-3' | 10 |
| VWA | 5'-GCCCTAGTGGATGATAAGAATAATCAGTATGTG-3' | 11 |
|  | 5'-GGACAGATGATAAATACATAGGATGGATGG-3' | 12 |
| D3S1358 | 5'-ACTGCAGTCCAATCT GGGT-3' | 13 |
|  | 5'-ATGAAATCAACAGAGGCTTG-3' | 14 |
| D3S1358 | 5'-ACTGCAGTCCAATCTGGGT-3' | 15 |
|  | 5'-ATGAAATCAACAGAGGCTTGC-3' | 16 |
| D5S818 | 5'-GGTGATTTTCCTCTTTGGTATCC-3' | 17 |
|  | 5'-AGCCACAGTTTACAACATTTGTATCT-3' | 18 |
| D5S818 | 5'-GGGTGATTTTCCTCTTTGGT-3' | 19 |
|  | 5'-TGATTCCAATCATAGCCACA-3' | 20 |
| D7S802 | 5'-ATGTTGGTCAGGCTGACTATG-3' | 21 |
|  | 5'-GATTCCACATTTATCCTCATTGAC-3' | 22 |
| D7S802 | 5'-TGTCATAGTTTAGAACGAACTAACG-3' | 23 |
|  | 5'-CTGAGGTATCAAAAACTCAGAGG-3' | 24 |
| D8S1179 | 5'-TTTTTGTATTTCATGTGTACATTCG-3' | 25 |
|  | 5'-CGTAGCTATAATTAGTTCATTTTCA-3' | 26 |
| D8S1179 | 5'-ATTGCAACTTATATGTATTTTTGTATTTCATG-3' | 27 |
|  | 5'-ACCAAATTGTGTTCATGAGTATAGTTTC-3' | 28 |
| D13S317 | 5'-ATTACAGAAGTCTGGGATGTGGAGGA-3' | 29 |
|  | 5'-GGCAGCCCAAAAAGACAGA-3' | 30 |

TABLE 1-continued

Primer Pairs for STR Loci

| STR locus | Primer Pair | SEQ ID NO: |
|---|---|---|
| D13S317 | 5'-ACAGAAGTCTGGGATGTGGA-3' | 31 |
|  | 5'-GCCCAAAAAGACAGACAGAA-3' | 32 |
| D16S539 | 5'-GGGGGTCTAAGAGCTTGTAAAAAG-3' | 33 |
|  | 5'-GTTTGTGTGTGCATCTGTAAGCATGTATC-3' | 34 |
| D16S539 | 5'-GATCCCAAGCTCTTCCTCTT-3' | 35 |
|  | 5'-ACGTTTGTGTGTGCATCTGT-3' | 36 |
| D18S51 | 5'-CAAACCCGACTACCAGCAAC-3' | 37 |
|  | 5'-GAGCCATGTTCATGCCACTG-3' | 38 |
| D18S51 | 5'-TTCTTGAGCCCAGAAGGTTA-3' | 39 |
|  | 5'-ATTCTACCAGCAACAACACAAATAAAC-3' | 40 |
| D21S11 | 5'-GTGAGTCAATTCCCCAAG-3' | 41 |
|  | 5'-GTTGTATTAGTCAATGTTCTCC-3' | 42 |
| D21S11 | 5'-ATATGTGAGTCAATTCCCCAAG-3' | 43 |
|  | 5'-TGTATTAGTCAATGTTCTCCAG-3' | 44 |
| D21S11 | 5'-ATATGTGAGTCAATTCCCCAAG-3' | 45 |
|  | 5'-TGTATTAGTCAATGTTCTCCAGAGAC-3' | 46 |
| D2S1338 | 5'-CAGTGGATTTGGAAACAGAAATG-3' | 47 |
|  | 5'-TCAGTAAGTTAAAGGATTGCAGG-3' | 48 |
| D19S433 | 5'-CCTGGGCAACAGAATAAGAT-3' | 49 |
|  | 5'-TAGGTTTTTAAGGAACAGGTGG-3' | 50 |
| AMEL | 5'-ACCTCATCCTGGGCACCCTGG-3' | 51 |
|  | 5'-AGGCTTGAGGCCAACCATCAG-3' | 52 |
| AMEL | 5'-ACCTCATCCTGGGCACCCTGGTT-3' | 53 |
|  | 5'-AGGCTTGAGGCCAACCATCAG-3' | 54 |

Suitable oligonucleotide primers for amplification can be selected based, for example, on the nucleic acid sequence of the flanking regions of the target sequence (e.g. regions flanking STR region(s)). Typically, oligonucleotide primers are approximately 12-25 nucleotides in length, but their size may vary considerably depending on such parameters as, for example, the base composition of the template sequence to be amplified, amplification reaction conditions, etc. Oligonucleotide primers can be designed to anneal to specific portions of DNA that flank a STR region of interest, to specifically amplify the portion of DNA between the primer-complementary sites. The length of the primer may need to be modified in order to be more specific and prevent amplification of non-target nucleic acid.

Oligonucleotide primers may include adenosine, thymidine, guanosine, and cytidine, as well as uracil, nucleoside analogs (for example, but not limited to, inosine, locked nucleic acids (LNA), non-nucleotide linkers, peptide nucleic acids (PNA) and phosporamidites) and nucleosides containing or conjugated to chemical moieties such as radionuclides, fluorescent molecules, minor groove binders (MGBs), or any other nucleoside conjugates known in the art.

Primers can be selected by the use of any of various software programs available and known in the art for amplification and/or multiplex amplification systems. The selected primers can be chemically synthesized.

Reagents of a standard amplification reaction, e.g., PCR reaction can include a solvent, DNA polymerase, deoxyribonucleoside triphosphates (dNTPs), oligonucleotide primers (a primer pair), a divalent metal ion, e.g., $MgCl_2$, $MgSO_4$ and the like, and a DNA sample that contains the target STRs. In some cases, the solvent is water with a buffering agent and non-buffering salts such as KCl. The buffering agent can be any buffer known in the art, such as, but not limited to, Tris-HCl, and can be varied by routine experimentation to optimize PCR results. Those of ordinary skill in the art recognize how to determine optimal buffering conditions. PCR buffers can be optimized depending on the particular polymerase or enzyme used for amplification.

PCR cycle temperatures, the number of cycles and their durations can be varied to optimize a particular amplification reaction as a matter of routine experimentation. Temperatures and cycle times are determined for three stages in PCR: denaturation, annealing and extension. One round of denaturation, annealing and extension is referred to as a "cycle." In standard PCR, the annealing temperature can be about 5-10° C. below the estimated $T_m$ of the least stable primer-template duplex. The annealing time can be between about 30 seconds and about 2 minutes. The annealing phase is generally followed by an extension phase. Extension can be conducted for a sufficient amount of time to allow the polymerase enzyme to complete primer extension into the appropriately sized amplification products. The number of cycles in a PCR reaction (one cycle includes denaturation, annealing and extension) determines the extent of amplification and the subsequent amount of amplification product. PCR results in an exponential amplification of DNA molecules. The number of cycles used can depend on the nature of the template sample. Those of skill in the art may adjust both cycle numbers and specific details of temperature and time intervals in order to optimize the reaction conditions.

Detailed descriptions of PCR amplification methods for STR regions are found in, e.g., U.S. Pat. Nos. 5,843,660; 6,221,598; 6,479,235; 7,008,771; 8,580,505, the disclosures of which are herein incorporated by reference in their entirety for all purposes. Methods and kits for performing multiplex amplification of STR regions are described in, e.g., U.S. Patent Application Nos. 2009/0142764, 2011/0306505, 2012/0122093, 2012/0309637, and 2014/0065613, and PCT International Application Publication No. WO2014/039997, the disclosures of which are herein incorporated by reference in their entirety for all purposes. Useful kits and systems for multiplex amplification of STR regions include Powerplex® 16 System (Promega), Powerplex 21® System (Promega), Powerplex® ES System (Promega), Powerplex® Fusion System (Promega), Investigator® IDplex Plus kit (Qiagen), Investigator® ESSplex SE Plus kit (Qiagen), Mentype® NonaplexQS twin (Biotype), Mentype® Chimera® (Biotype), Genome Lab™ Human STR Primer Set (Beckman Coulter), AmpF1STR® SGM Plus® PCR Amplification Kit (Thermo Fisher), AmpF1STR® Identifiler® PCR Amplification Kit (Thermo Fisher), AmpF1STR® Globalfiler® PCR Amplification Kit (Thermo Fisher), AmpFlSTR® Profiler Plus® PCR Amplification Kit (Thermo Fisher), and the like.

Upon amplification of the nucleic acid template containing one or more target sequences (e.g. selected STR alleles) using a primer pair specific to the selected loci or alleles, amplicons or amplification products that are specific to each allele (e.g. STR allele) are produced. The amplicons representing a specific allele is then sequenced to determine a signature sequence and/or the number of repeat units in said allele.

It will be understood that PCR amplification methods such as those set forth above and elsewhere herein are exemplary. Any of a variety of known amplification techniques can be used to increase the amount of nucleic acid sequences present for use in a method set forth herein. Exemplary techniques include, but are not limited to, polymerase chain reaction (PCR), rolling circle amplification (RCA), multiple displacement amplification (MDA), or random prime amplification (RPA) of nucleic acid molecules having template sequences. It will be understood that amplification of target nucleic acids prior to use in a method or composition set forth herein is optional. As such, target nucleic acids will not be amplified prior to use in some embodiments of the methods and compositions set forth herein. Solid-phase amplification methods can also be used, including for example, cluster amplification, bridge amplification, solid-phase PCR, solid-phase RCA, solid-phase MDA or other methods that utilize support-bound primers to capture and/or prime synthesis of nucleic acids. Rolling circle amplification (RCA) can be carried out, for example, as described in Lizardi et al., *Nat. Genet.* 19:225-232 (1998) or US Pat. App. Pub. No. 2007/0099208 A1, each of which is incorporated herein by reference. Exemplary methods for cluster amplification are set forth, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

Provided herein is a method of sequencing repeat regions (e.g. STR amplicons or STR amplification products described above) to count the repeat units (e.g. the number of specific STR units) in the amplicons. Useful sequencing platforms include sequencing-by-synthesis (sequencing-by-incorporation), pH-based sequencing, sequencing by polymerase monitoring, and other methods of massively parallel sequencing or next-generation sequencing.

Sequencing-by-synthesis (SBS) techniques generally involve the enzymatic extension of a nascent nucleic acid strand through the iterative addition of nucleotides against a template strand. SBS can utilize nucleotide monomers that have a terminator moiety or those that lack any terminator moieties. Methods utilizing monomers having terminators include, for example, those described in WO 04/018497, U.S. Pat. No. 7,057,026, WO 91/106678, WO 07/123744, US 2007/0166705, US 2006/0188901, US 2006/0240439, US 2006/0281109, WO 05/065814, US 2005/0100900, WO 06/064199 or WO 07010251, the disclosures of which are incorporated herein by reference in their entireties. Also useful are SBS methods that are commercially available from Illumina, Inc., San Diego Calif.

Optionally, the sequencing is carried out as described in commonly owned U.S. Ser. No. 14/805,381, which is incorporated by reference herein in its entirety. Briefly, methods for determining the sequence of a template nucleic acid molecule can be based on formation of a ternary complex (between polymerase, primed nucleic acid and cognate nucleotide) under specified conditions. The method can generally include an examination step prior to incorporation of a nucleotide. The examination step can involve providing a template nucleic acid molecule primed with a primer; contacting the primed template nucleic acid molecule with a first reaction mixture that includes a polymerase and at least one nucleotide molecule; monitoring the interaction of the polymerase with the primed template nucleic acid molecule in the presence of the nucleotide molecule, without chemical incorporation of the nucleotide molecule into the primed template nucleic acid; and identifying a next base in the template nucleic acid using the monitored interaction of the polymerase with the primed template nucleic acid molecule in the presence of the nucleotide molecule. In this procedure, ternary complex stabilization and binary complex destabilization advantageously enhance discrimination between correct and incorrect nucleotides.

The sequencing method provided herein can include a series of nucleic acid incorporation steps and nucleic acid examination steps. In some cases, the one or more incorporation steps are performed prior to an examination step. In other cases, one or more incorporation steps are performed after an examination step. Optionally, more incorporation steps are performed than examination steps. As such, the number of incorporations executed can be greater than the number of examinations. Thus, the number of nucleotides added to a primer by extension can be greater than the number of examination steps carried out during the primer extension.

To begin the sequencing method in some embodiments, a capture primer that is complementary to the template strand is annealed to the template strand. In some cases the template strand is the sense strand of the STR locus or alternatively, the template strand is the antisense strand of the STR locus. As such, the capture primer determines whether the sense strand and/or antisense strand that contains the STR locus is sequenced. The template strand can be an amplicon, e.g., a product of an amplification reaction. The capture primer can be attached to a solid support such as a solid surface or bead. Exemplary solid supports include, but are not limited to arrays that provide a population of different molecules attached to one or more solid-phase substrates such that the different molecules can be differentiated from each other according to their relative location. An array can include different molecules that are each located at a different addressable location on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream. The molecules of the array can be nucleic acid primers, nucleic acid probes, nucleic acid templates or nucleic acid enzymes such as polymerases.

A subset of nucleic acid base types such as three or fewer nucleic acid base types (e.g., A and T and C, A and T, or A) can be incorporated under proper conditions into a growing strand (i.e., a complementary strand that is opposite the template strand) that is an extension of the capture primer. The subset of nucleic acid base types can be selected based on the known sequence of a specific STR region. For example, with an STR region having a repeat unit of [AATG] and the subset of nucleic acid bases for incorporation into the growing strand can be A and T. In particular embodiments, a subset of nucleic acid base types will exclude nucleotides that are expected to complement at least one species of nucleotide in a repeated sequence (e.g. an STR repeat unit). For example, a subset of nucleic acid base types used in a method of the present disclosure can exclude nucleic acid base types that are expected to complement 1, 2 or 3 species of nucleic acid base types in a repeat unit, so long as the subset includes a base type that complements at least one type of base in the repeat unit.

The capture primer can be used to capture the template strand. Optionally, the capture primer can also be used as the sequencing primer. In some cases, a capture primer captures the template strand and a sequencing primer that has a different sequence than the capture primer initiates sequencing, or another method known in the art for determining the sequence of a nucleic acid template.

The number of repeating units of the STR region can be determined using a sense strand or antisense strand of the nucleic acid of the sample or of the amplification product derived from the sample. The method provided herein can be used to analyze the sense strand, the antisense strand, or both.

The subset of nucleic acid base types can include 1 nucleic acid base type, 2 nucleic acid base types or 3 nucleic acid base types. Optionally, the subset of nucleic acid base types comprises one nucleic acid base type. The subset of nucleic acid base types can consist of one nucleic acid base type. Alternatively, the subset of nucleic acid base types comprises two nucleic acid base types. The subset of nucleic acid base types can consist of two nucleic acid base types. The subset of nucleic acid base types can include nucleic acid base types that are expected to complement at least one base type present in a repeat unit but no more than 1, 2 or 3 base types present in the repeat unit.

The subset of nucleic acid base types can comprise adenine base types and thymine base types. Optionally, the subset of nucleic acid base types comprises cytosine base types and thymine base types. Optionally, the subset of nucleic acid base types comprises guanine base types and thymine base types. Optionally, the subset of nucleic acid base types comprises adenine base types and guanine base types. Optionally, the subset of nucleic acid base types comprises adenine base types and cytosine base types. Optionally, the subset of nucleic acid base types comprises guanine base types and cytosine base types.

Optionally, the subset of nucleic acid base types can complement adenine base types and thymine base types. Optionally, the subset of nucleic acid base types can complement cytosine base types and thymine base types. Optionally, the subset of nucleic acid base types can complement guanine base types and thymine base types. Optionally, the subset of nucleic acid base types can complement adenine base types and guanine base types. Optionally, the subset of nucleic acid base types can complement adenine base types and cytosine base types. Optionally, the subset of nucleic acid base types can complement guanine base types and cytosine base types.

The preselected nucleic acid base type can be a guanine base type, thymine base type, cytosine base type, or adenine base type. The preselected nucleic acid base can be an adenine, cytosine, guanine or thymine, depending on the target sequence (e.g. STR region). The selection of the specific nucleic acid can depend on nucleic acid sequence of the allele or locus of the target nucleic acid (e.g. the repeat unit of the STR allele) or the reverse complement thereof and the subset of the nucleic acid bases.

The preselected nucleic acid base type may be labeled. Optionally, the subset of nucleic acid base types includes one or more unlabeled nucleic acid base types. Alternatively, the subset of nucleic acid base types comprises differentially labeled nucleic acid base types. In other words, each nucleic acid base type can have a different detectable label. The label may be chemically attached to the nucleic acid base. Optionally, the subset of nucleic acid base types lack a detectable label and the preselected base type comprises a detectable label. Optionally, the subset of nucleic acid base types and preselected base types lack a detectable label, e.g., a fluorescent label.

Next, a preselected nucleic acid base can be incorporated into the growing strand. Preferably, the incorporated nucleotide does not include an exogenous label (e.g. the nucleotide does not include an optical moiety such as a fluorophore or Raman label). The preselected nucleic acid base is different than any one of the subset of nucleic acid base types. For instance, if the subset of nucleic acid bases is A and T, the preselected nucleic acid base cannot be A or T, but can be C or G. The subset of nucleic acid bases used to an STR allele containing [AATG] can be A and T, and the preselected nucleic acid base can be G. Accordingly, the preselected nucleic acid base will be complementary to nucleotides of a repeat region that are not complemented by the subset of nucleic acid base types.

The incorporation step is performed using a polymerase and under conditions to add the preselected nucleic acid base to the growing strand. Optionally, the incorporation step is 30-60 seconds.

After incorporating the subset of bases and/or the preselected base, a method set forth herein can include a step of separating reaction components, for example, by washing with a wash buffer. In some cases, the washing buffer contains one or more of the following reagents: EDTA, a salt, e.g., KCl, a detergent, e.g., Tween-20, and a buffer. Washing may be under conditions that do not disturb the hybridization of the template strand of the amplicon to either the capture primer or the growing strand extending from the capture primer.

The presence of a preselected nucleic acid base can be detected and counted in an examination step that is carried out prior to an incorporation step. As such, the examination step and incorporation step can employ nucleotides having the same type of base; however, the conditions or reagents used in the steps can differ with regard to inhibiting (in the former step) or promoting (in the latter step) formation of a phosphodiester bond between next correct nucleotide and primed nucleic acid. The examination step can be for 5-120 seconds, e.g., 5 seconds, 10 seconds, 20 seconds, 30 seconds, 40 seconds, 50 seconds, 60 seconds, 90 seconds or 120 seconds. The detecting step can include detecting a ternary complex formed by the polymerase, the preselected nucleic acid base type and the template strand of target nucleic acid (e.g. template strand of an STR amplification product or STR amplicon). The detecting step can be carried out, for example, as described in commonly owned U.S. Ser. No. 14/805,381, which is incorporated herein by reference. Alternatively, the preselected base type is detected by detecting a labeled polymerase included in the mix comprising the preselected base type. Following the examination step, additional rounds or cycles that include incorporating the subset of nucleic acid bases, incorporating the preselected nucleic acid base, and examining the preselected base can be performed until a desired signature is identified or until the maximum number of repeat units present in a repeat region (e.g. in an STR allele) is detected.

The steps of incorporating the subset of nucleic acid bases and the preselected nucleic acid base can be performed for at least 3, 4, 5, 6, 7, 8, 9, 10, 11, 12, 13, 14, 15, 16, 17, 18, 19, 20 or more rounds before the preselected nucleic acid base at the 3' end of the growing strand is detected or counted.

It will be understood that for methods that employ polymerases at multiple steps, each step can employ the same type of polymerase or different types of polymerases can be used for different steps. For example, the same type of polymerase can be used to form a stable ternary complex in one step and to perform an extension reaction in another step. Nevertheless, this same type of polymerase can be subjected to different conditions or different nucleotide analogs to selectively promote or inhibit extension activity. Alternatively, a first polymerase type can be used to form a ternary complex and a different polymerase type can be used for an extension step. For example, the different polymerases can have different nucleotide binding properties or different catalytic rates for extension that favor their use in either step.

The present disclosure provides a method for determining number of repeats of a short tandem repeat (STR) region in a sample, the method comprising: (a) contacting an STR product comprising a template strand to be sequenced with a capture primer complementary to the template strand, wherein the STR product comprises one or more STR repeat units; (b) incorporating a subset of nucleic acid base types into a complementary strand opposite the template strand by extending the capture primer; (c) incorporating a preselected nucleic acid base type that is different than the subset of nucleic base types of step (b) into the complementary strand; and (d) detecting the presence of the preselected nucleic acid base type in the complementary strand, thereby determining the number of STR repeat units in the STR region. Steps (b) and (c) of the method can be repeated for at least 3, 4, 5, 6, 7, 8, 9, 10, 11, 12 or 13 rounds before step (d). Optionally, steps (b) and (c) are repeated until the preselected nucleic acid base type is not detected in the complementary strand. Optionally, steps (b) and (c) are repeated for at least 3, 4, 5, 6, 7, 8, 9, 10, 11, 12 or 13 rounds before step (d). Optionally, steps (b) and (c) are repeated for at least 12 rounds before step (d).

For instance, for an STR region that may contain between 6-15 [AATG] repeats, 5 rounds of A, T and G incorporation may occur without detecting the presence of a G base at the end of the growing strand. At the $6^{th}$ round and subsequent rounds thereafter, a single round can include adding A and T bases to the growing strand, and adding and detecting a G base. Rounds can be performed until the G base is no longer detected in the growing strand.

Optionally, the step of incorporating the subset of nucleic acid bases and the preselected nucleic acid base followed by the step of examining or detecting the presence of the preselected base represents a round or cycle of the sequencing reaction. As such, the method disclosed herein can include performing at least 3, 4, 5, 6, 7, 8, 9, 10, 11, 12, 13, 14, 15, 16, 17, 18, 19, 20 or more rounds before counting the number of times the preselected base has been detected in the growing strand. The number of rounds can be selected based on the expected number of repeat units for a target STR allele.

The number of rounds of examining can be less than the number of possible repeat units for a specific STR allele or other repeat region. For example, if the repeat unit number is 10, the number of times step (c) of the method described herein is performed can be 8 or less. Optionally, the number of rounds of examining can be equal to the number of possible repeat units. Optionally, the number of rounds of examining can be greater than the number of possible repeat units for a specific STR allele or other repeat region. For example, if the repeat unit number is 10, the number of times step (c) is performed can be 12 or more.

The subset of nucleic acid base types can be the same in each round of the sequencing reaction. Optionally, the subset of nucleic acid base types is the same for 1, 2, 3, 4, 5, 6, 7, 8, 9, 10, 11, 12, 13, 14, 15, 16, 17, 18, 19, 20 or more rounds. Optionally, the subset of nucleic acid base types is different between rounds of the sequencing reaction. For instance, the subset of nucleic acid base types can be different in each round or in alternating rounds. The subset of nucleic acid base types may be different for 1, 2, 3, 4, 5, 6, 7, 8, 9, 10, 11, 12, 13, 14, 15, 16, 17, 18, 19, 20 or more rounds.

The preselected nucleic acid base type can be the same in each round. Optionally, the preselected nucleic acid base type is the same for 1, 2, 3, 4, 5, 6, 7, 8, 9, 10, 11, 12, 13, 14, 15, 16, 17, 18, 19, 20 or more rounds. Optionally, the preselected nucleic acid base type is different between rounds. Optionally, the preselected nucleic acid base type can be different in each round or in alternating rounds. The preselected nucleic acid base type may be different for 1, 2, 3, 4, 5, 6, 7, 8, 9, 10, 11, 12, 13, 14, 15, 16, 17, 18, 19, 20 or more rounds.

The subset of nucleic acid base types and the preselected nucleic acid base type are chosen based on whether the sense or antisense strand of the template strand is interrogated. The template strand can include the STR loci or the reverse complement thereof.

Optionally, the examination step include detecting the presence of a complex formed by a polymerase, the preselected nucleic acid base, and the template strand that contains the target STR allele or a reverse complement thereof.

The numbered, cross referenced sections below provide further exemplary embodiments.

1. The present disclosure provides a method for determining number of repeats of a short tandem repeat (STR) region in a sample, the method comprising: (a) contacting an STR product comprising a template strand to be sequenced with a capture primer complementary to the template strand, wherein the STR product comprises one or more STR repeat units; (b) incorporating a subset of nucleic acid base types into a complementary strand opposite the template strand by extending the capture primer; (c) incorporating a preselected nucleic acid base type that is different than the subset of nucleic base types of step (b) into the complementary strand; and (d) detecting the presence of the preselected nucleic acid base type in the complementary strand, thereby determining the number of STR repeat units in the STR region.

2. The method set forth in 1, further comprising amplifying nucleic acids in the sample with a composition comprising a primer pair specific for the STR region to produce the STR product before performing step (a).

3. The method set forth in 1, wherein determining the number of STR repeat units comprises determining the frequency that the preselected nucleic acid base type is incorporated into the complementary strand.

4. The method set forth in 1, wherein step (d) comprises detecting a ternary complex formed by the polymerase, the preselected nucleic acid base type and the template strand.

5. The method set forth in 1, wherein steps (b) and (c) are repeated for at least 3, 4, 5, 6, 7, 8, 9, 10, 11, 12 or 13 rounds before step (d).

6. The method set forth in any of 1 to 5, wherein steps (b) and (c) are repeated until the preselected nucleic acid base type is not detected in the complementary strand.

7. The method set forth in 6, wherein steps (b) and (c) are repeated for at least 3, 4, 5, 6, 7, 8, 9, 10, 11, 12 or 13 rounds before step (d).

8. The method set forth in 6, wherein steps (b) and (c) are repeated for at least 12 rounds before step (d).

9. The method set forth in 5, wherein the subset of nucleic acid base types of step (b) is the same in each round.

10. The method set forth in 5, wherein the subset of nucleic acid base types of step (b) is different in each round.

11. The method set forth in 1, further comprising a wash step with a wash buffer.

12. The method set forth in 1, wherein the subset of nucleic acid base types comprises one nucleic acid base type.

13. The method set forth in 1, wherein the subset of nucleic acid base types comprises two nucleic acid base types.

14. The method set forth in 13, wherein the two nucleic acid base types comprise adenine base types and thymine base types.

15. The method set forth in 13, wherein the two nucleic acid base types comprise cytosine base types and thymine base types.

16. The method set forth in 13, wherein the two nucleic acid base types comprise guanine base types and thymine base types.

17. The method set forth in 13, wherein the two nucleic acid base types comprise adenine base types and guanine base types.

18. The method set forth in 13, wherein the two nucleic acid base types comprise adenine base types and cytosine base types.

19. The method set forth in 13, wherein the two nucleic acid base types comprise guanine base types and cytosine base types.

20. The method set forth in 1, wherein the preselected nucleic acid base type is a guanine base type, thymine base type, cytosine base type, or adenine base type.

21. The method set forth in any of 1 to 20, wherein the preselected nucleic acid base type is labeled.

22. The method set forth in 21, wherein the subset of nucleic acid base types subset comprises unlabeled nucleic acid base types.

23. The method set forth in any of 1 to 20, wherein the subset of nucleic acid base types comprises differentially labeled nucleic acid base types.

24. The method set forth in 1, wherein the capture primer is attached to a solid surface.

25. The method set forth in any of 1 to 24, wherein the STR region is a CODIS allele, a SGM+ allele, or a sex determination allele.

26. The method set forth in 25, wherein the CODIS allele is selected from the group consisting of CSF1PO, FGA, TH01, TPOX, VWA, D3S1358, D5S818, D7S802, D8S1179, D13S317, D16S539, D18S51, and D21S11.

27. The method set forth in 25, wherein the SGM+ allele is selected from the group consisting of FGA, TH01, VWA, D2S1338, D3S1358, D8S1179, D16S539, D18S51, D19S433, and D21S11.

28. The method set forth in any of 1 to 25, wherein the STR region has the STR repeat unit selected from the group consisting of AAAG, AAAGA, AAGG, TAGG, AATG, AGAT, AGAC, ATT, CTTT, GAAA, GATA, GGAA, TAGA, TCTA, TCAA, TGCC, TTCC, TCTG, or a reverse complement thereof.

29. The method set forth in 28, wherein if the STR repeat unit is AGAT, AATG, GATA, or GAAA, the subset of nucleic acid base types are adenine base types and thymine base types and the preselected base type is a guanine base type; the subset of nucleic acid base types are adenine base types and guanine base types and the preselected base type is a thymine base type; or the subset of nucleic acid base types are thymine base types and guanine base types and the preselected base type is a adenine base type 30. The method set forth in 25, wherein the sex determination allele is amelogenin (AMEL).

31. The method set forth in 30, wherein the subset of nucleic acid base types are adenine base types and guanine base types and the preselected nucleic acid base type is a thymine base type.

EXAMPLES

The following examples are offered to illustrate, but not to limit, the claimed invention.

Example 1

Methods for Rapid Detection and Analysis of Short Tandem Repeat (STR) Allelic Variations STR analysis is used for a variety of applications such as genotyping, identity testing, lineage analysis and forensics. The United States Federal Bureau of Investigation (FBI) has established and maintains a Combined DNA Index System (CODIS), a database of DNA typing information that is used to match forensic DNA evidence collected at crime scenes with DNA information in the database. Currently the FBI includes 13 polymorphic STR regions in the CODIS database (FIG. 1) including CSF1PO, FGA, TH01, TPOX, VWA, D3S1358, D5S818, D7S820, D8S1179, D13S317, D16S539, D18S51, and D21S11. An STR region is a series of 3-27 repeat units on a DNA strand where each repeat unit is represented by a core repeat pattern such as a di-, tri-, tetra-, penta-, or hexa-nucleotide base unit. The specific number of repeating units for each STR region varies for each individual. As such, individuals can be identified based by their allelic variations in the 13 STR regions of the CODIS database. In some cases, a sex determination STR region such as amelogenin is also used to determine an individual's identity.

Traditional analysis of the number of repeat units at a particular STR region is performed by determining the size of a PCR amplicon of the selected STR region. PCR primers are designed to fit outside of the STR region such that the resulting PCR amplicon represents the number of STR repeat units. For each STR region, longer fragments correspond to more repeat units. For the core CODIS STR regions, each repeat unit is 4 nucleotide bases; a difference of three STR repeat units results in amplicon that are different in size by 12 nucleotide bases, a difference of five STR repeat units results in amplicons that are different in size by 20 nucleotide base, and so on.

The standard sequencing method for STR determination is to insert the STR amplicon directly into a standard workflow. This method results in examining each position in the STR amplicon multiple times to determine the sequence of the STR amplicon. For an STR region with a repeat 4-nucleotide base unit, 16 examination steps are required to determine the identity of each of the 4 bases of a single repeat unit.

This example provides a method that can accurately and directly determine the number of repeat units of a STR region without examining each nucleotide base of a repeat unit. The method is based, in part, on the discovery that a single preselected base of an STR repeat unit can be examined to determine the presence of an STR repeat unit in a nucleic acid sample. For instance, the method disclosed herein can be used to count the number of repeat at the STR locus TPOX that has a repeat unit of [AATG] by sequencing and performing an examining step for the presence of "G" in the repeat unit. Each "G" found represents a single TPOX repeat unit. The other nucleotide bases such as "A" and "T" of the TPOX locus are incorporated in the growing strand during sequencing, but not examined or detected. Typically, the examination step is a rate-limiting step during sequencing because it can take minutes to complete, while incorporation of nucleotide bases occurs much faster and on the order of seconds.

As described above, allelic variations in specific STR regions can include between 3-27 repeat units, or in some cases between 6-14 repeat units. In such instances, if fewer than x number of repeat units is not expected in the nucleic acid sample, then the first (x−1) repeat units can be incorporated and not examined during sequencing. The presence of a preselected base in the x repeat unit and subsequent repeat units can be examined and counted. An exemplary example is provided herewith. The STR region has a series of 6 to 14 repeat units with each unit having a nucleotide sequence of [AATG]. The method provided herein includes (1) incorporating the nucleotide bases for the first 5 repeated units of the STR region without an examination step, (2) incorporating the "A" and "T" nucleotide bases for the $6^{th}$ repeated unit, (3) incorporating the "G" nucleotide base for the $6^{th}$ repeated unit, (4) examining the "G" nucleotide base for the $6^{th}$ repeat unit, and (5) repeat steps (2) and (4) until all the repeated units of the TPOX region are counted.

It should be noted that some STR regions do not include all standard nucleotide base types such as adenine, thymine, cytosine and guanine. For example, the STR region FGA has a repeat unit of [CTTT] and the STR region VWA has a repeat unit of [TCTA]. In such instances, a guanine base type or "G" can be excluded from the reagents used in the examination step of sequencing.

A. Methods for Detecting STR Region TPOX

In this experiment the number of TPOX repeating units [AATG] was counted in two different synthetic DNA templates: (1) a template with 5 TPOX repeats (TPOX-5; SEQ ID NO:55; GTTTATTGCCCAAACATTCATTCATTCATTCATTCAGTGAGGGTTCCCTAAGTGCCTG TTCTGTGCCAGT) and (2) a template with 9 TPOX repeats (TPOX-9; SEQ ID NO:56; GTTTATTGCCCAAACATTCATTCATTCATTCATTCATTCATTCATTCAGTGAGG GTTCCCTAAGTGCCTGTTCTGTGCCAGT). A synthetic TPOX primer (SEQ ID NO:57; ACTGGCACAGAACAGGCACTTAGGGAACCCTCACTG) was used to anneal to a region of the synthetic DNA templates outside of the STR region. The synthetic primer is reverse complementary to a portion of the synthetic TPOX-5 and TPOX-9 templates. A sequencing primer or probe was used for sequencing by incorporation to determine the number of TPOX repeats in the TPOX-5 and TPOX-9 templates.

The synthetic primer was modified with biotin on the 5' end to allow it to bind to a biosensor on a detection instrument that can directly measure biomolecular interactions. In this experiment an Octet® platform from Pall ForteBio (Menlo Park, Calif.) was used. Each synthetic template was mixed with the primer (100 μM each) and hybridized. Each template-primer mixture was bound to the biosensors of the instrument for analysis. The biosensor tip was dipped into the solutions described in the table below in the following order for the indicated times.

TABLE 2

Sequencing Reaction for TPOX

| TPOX Step | Time (s) | |
|---|---|---|
| Bind DNA | 300 | |
| Wash | 30 | |
| Incorporate AT | 45 | repeat |
| EDTA Wash | 90 | |
| Wash | 30 | |
| Examine G | 90 | |
| Incorporate G | 45 | |
| EDTA Wash | 90 | |
| Wash | 30 | |

For the TPOX region, "A" and "T" nucleotide bases were incorporated and the preselected "G" nucleotide base was examined in each cycle of the sequencing reaction.

The compositions of the solutions provided in Table 2 are provided below in Table 3.

TABLE 3

Reagents for TPOX Sequencing Reaction

| Wash Buffer | |
|---|---|
| Tris pH 8.0 | 30 mM |
| KCl | 160 mM |
| K$_2$ glutamate | 160 mM Glu- |
| Tween-20 | 0.01% (v/v) |
| b-ME | 1.0 mM |
| BSA | 100 µg/mL |

| G Incorporation | |
|---|---|
| Tris pH 8.0 | 30 mM |
| KCl | 160 mM |
| K$_2$ glutamate | 160 mM Glu- |
| Tween-20 | 0.01% (v/v) |
| b-ME | 1.0 mM |
| BSA | 100 µg/mL |
| MgCl$_2$ | 2.0 mM |
| Bsu DNA Pol | 68 U/mL |
| dGTP | 100 µM |

| G Examination | |
|---|---|
| Tris pH 8.0 | 30 mM |
| KCl | 160 mM |
| K$_2$ glutamate | 160 mM Glu- |
| Tween-20 | 0.01% (v/v) |
| b-ME | 1.0 mM |
| BSA | 100 µg/mL |
| Ni(II)SO$_4$ | 1 mM |
| Bsu DNA Pol | 68 U/mL |
| dGTP | 100 µM |

| EDTA Wash | |
|---|---|
| Tris pH 8.0 | 30 mM |
| KCl | 160 mM |
| EDTA | 1.0 mM |
| Tween-20 | 0.01% (v/v) |
| b-ME | 1.0 mM |
| BSA | 100 µg/mL |

| A-T Incorporation | |
|---|---|
| Tris pH 8.0 | 30 mM |
| KCl | 160 mM |
| K$_2$ glutamate | 160 mM Glu- |
| Tween-20 | 0.01% (v/v) |
| b-ME | 1.0 mM |
| BSA | 100 µg/mL |
| MgCl$_2$ | 2.0 mM |
| Bsu DNA Pol | 68 U/mL |
| dATP | 25 µM |
| dTTP | 100 µM |

Figure 2A:
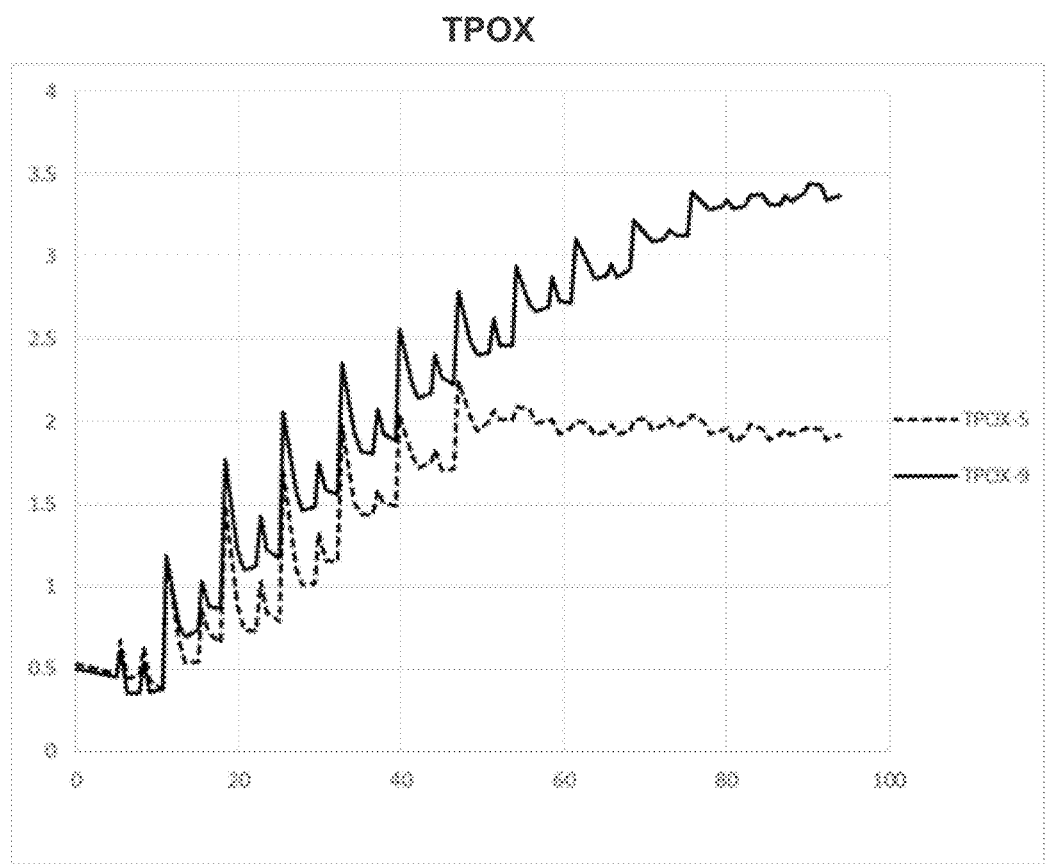
FIG. 2A and FIG. 2B are graphs showing results of an experiment for determining the number of repeat units at the TPOX loci in a sample containing a sequencing template with 5 repeats (TPOX-5; dashed line) and a sample containing a sequencing template with 9 repeats (TPOX-9; solid line).

FIG. 2A provides a trace of the sequencing reaction. The peaks indicate that a "G" nucleotide was detected in the template. The trace for the TPOX-5 template shows 6 peaks as expected. There are 5 "G" peaks from the 5 repeating units of TPOX-5 and a 6th "G" that represents the signal from the [GGG] in the flanking region outside of the repeating unit.

Figure 2B:
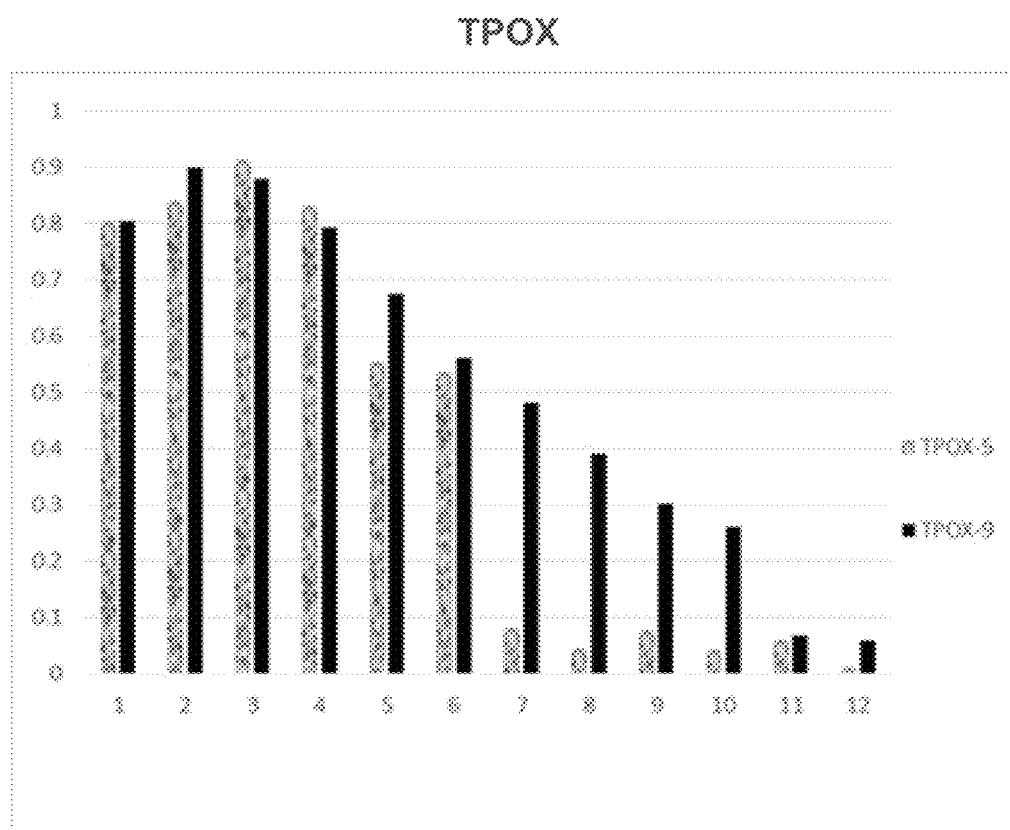

FIG. 2B provides a bar graph of the peak height for the reaction depicted in FIG. 2A. For the TPOX-5 template (gray bars), the 6 expected peaks, each representing the presence a "G" nucleotide base of the repeat, was detected. The signal strength significantly dropped at the first negative peak. Similarly, there were ten peaks for the TPOX-9 template (black bars), as expected, and a significant drop in the signal at peak 11.

A similar experiment was performed but this time three synthetic DNA templates were used. Specifically, the number of TPOX repeating units was determined in (1) the TPOX-5 template sample, (2) the TPOX-9 template sample, and (3) a sample mixture containing an equal amount of the TPOX-5 and TPOX-9 templates (TPOX-hetero). The same sequence reaction and solutions provided in Table 2 and Table 3 were used.

Figure 3A:
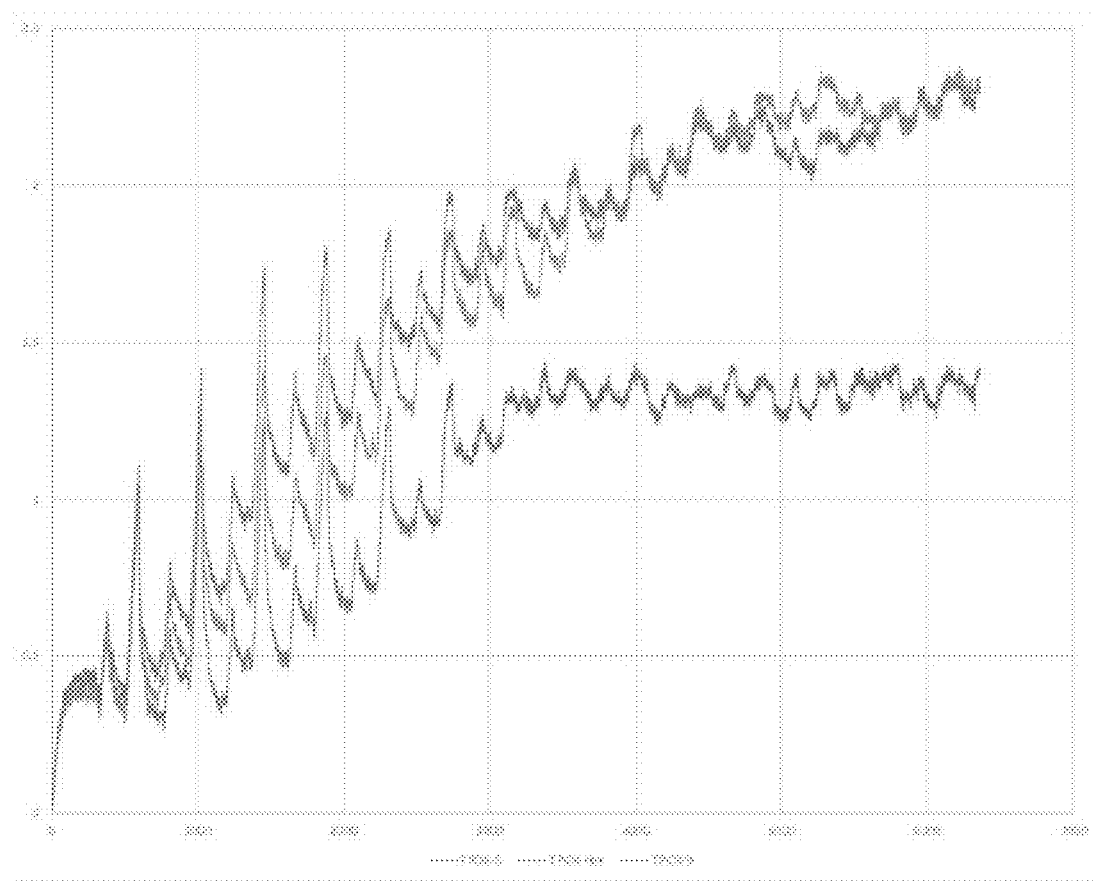
FIG. 3A and FIG. 3B are graphs showing results from an experiment for determining the number of repeat units in the TPOX loci in three different samples: (1) TPOX sequencing template with 5 repeats (TPOX-5); (2) TPOX sequencing template with 9 repeats; and (3) a mixture of TPOX-5 and TPOX-9 templates (TPOX-hetero).
Figure 3B:
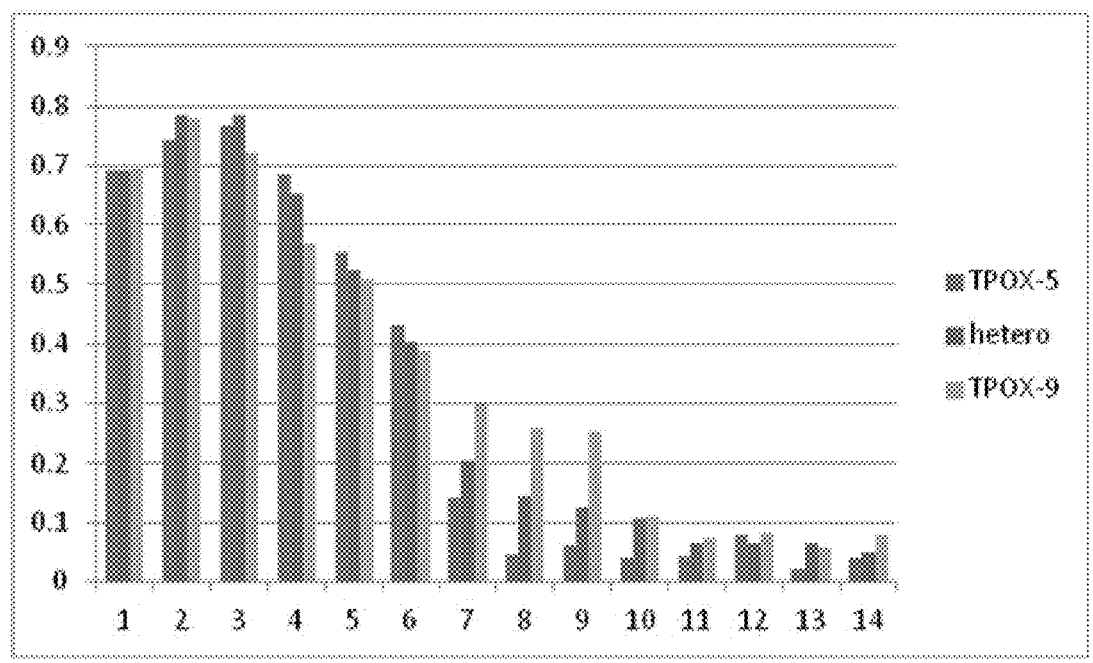

FIG. 3A shows the trace of the sequencing reaction and FIG. 3B provides a bar graph of the data. The results show that the signal for TPOX-5 was good and that 5 repeating TPOX units were counted. There was a decrease in signal for the TPOX-hetero sample after the detection of the TPOX-5 portion of the mixed sample was complete. The signal decay made it difficult to distinguish between the final positive peak and the first negative peak for TPOX-9 and TPOX-Hetero samples.

B. Methods for Detecting STR Region VWA

In the experiment the number of VWA repeating units [TCTA] was counted in two different synthetic DNA templates: (1) a template with 4 VWA repeats (VWA-4; SEQ ID NO:58; TGTCTGTCTATCTATCTATCTATCCATCTATC-CATCCATCCTATGTATTTATCATCTGT CC), (2) a template with 10 VWA repeats (VWA-10; SEQ ID NO:59; TGTCTGTCTATCTATCTATCTATCTATCTATCTATC-TATCTATCTATCCATCTATCCAT CCATCCTATGTATT-TATCATCTGTCC) and (3) a mixture containing equal portions of the VWA-4 and VWA-10 templates. A synthetic VWA primer (SEQ ID NO:60; GGACAGATGATAAATA-CATAGGATGGATGG) was used to anneal to a region of the synthetic DNA templates outside of the STR region. A sequencing primer or probe was used for sequencing by incorporation.

The synthetic VWA primer was modified with biotin on the 5' end to allow it to bind to a biosensor on a detection instrument. Each synthetic template was mixed with the primer (100 µM each) and hybridized. As described above, each template-primer mixture was bound to the biosensors of the instrument for analysis. The biosensor tip was dipped into the solutions described in the table below in the following order for the indicated times.

TABLE 4

Sequencing Reaction for VWA

| VWA Step | Time (s) |
|---|---|
| Bind DNA | 300 |
| Wash | 30 |
| Incorporate AT | 45 |
| EDTA Wash | 90 |
| Wash | 30 |
| Incorporate G | 45 |
| EDTA Wash | 90 |

TABLE 4-continued

Sequencing Reaction for VWA

| VWA Step | Time (s) | |
| --- | --- | --- |
| Wash | 30 | |
| Incorporate AT | 45 | |
| EDTA Wash | 90 | |
| Wash | 30 | |
| Incorporate G | 45 | |
| EDTA Wash | 90 | |
| Wash | 30 | |
| Incorporate AT | 45 | repeat |
| EDTA Wash | 90 | |
| Wash | 30 | |
| Examine G | 90 | |
| Incorporate G | 45 | |
| EDTA Wash | 90 | |
| Wash | 30 | |

The sequencing steps incorporated nucleotide bases from the end of the VWA primer and the start of the first repeating unit of the VWA region in order for the number of peaks detected by the instrument to correspond to the number of STR repeating units. Table 4 shows a series of incorporation steps prior to reaching the VWA region of the templates.

For the VWA region, "A" and "T" nucleotide bases were incorporated and the preselected "G" nucleotide base was examined in the sequencing reaction to count the VWA repeating units.

Figure 4A:
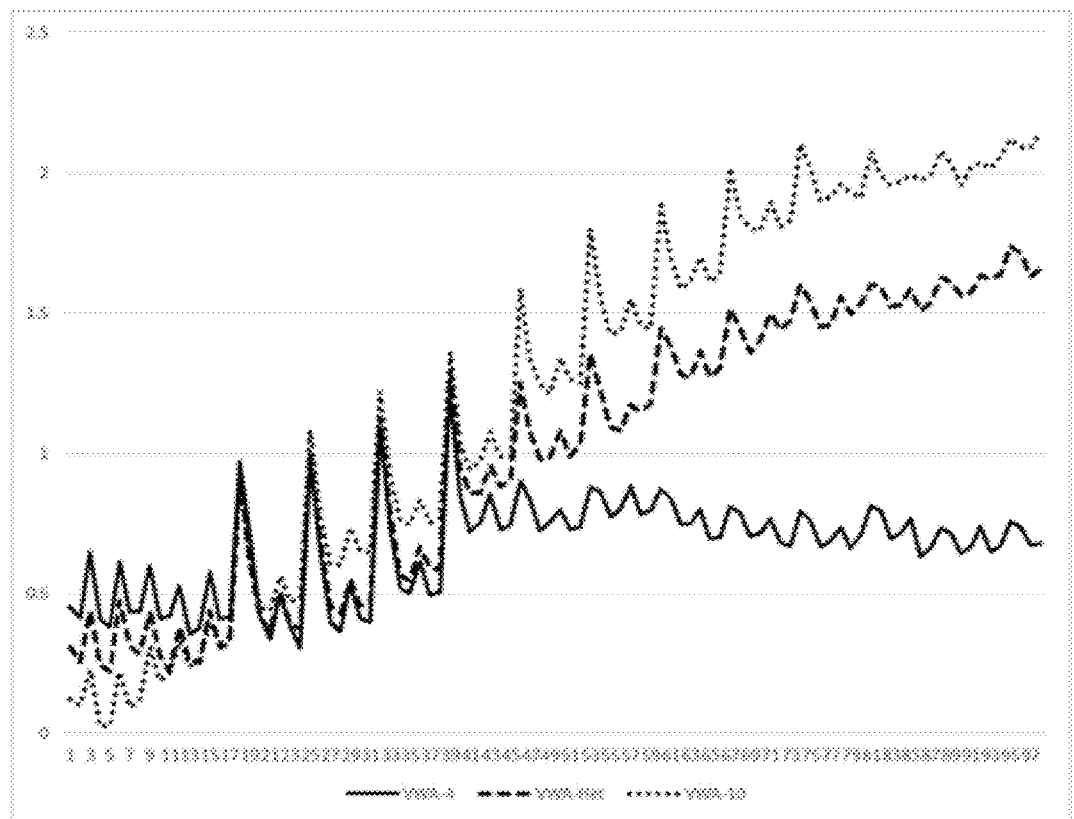
FIG. 4A and FIG. 4B are graphs showing results of an experiment for determining the number of repeat units at the VMA loci in three different samples: (a) sample containing a sequencing template with 4 repeats (VMA-4; solid line or black bar); (2) a sample containing a sequencing template with 10 repeats (VMA-10; dotted line or gray bar); and (3) a mixture of VMA-4 and VMA-10 templates (VMA-hetero; dashed lines or black-white bar).
Figure 4B:
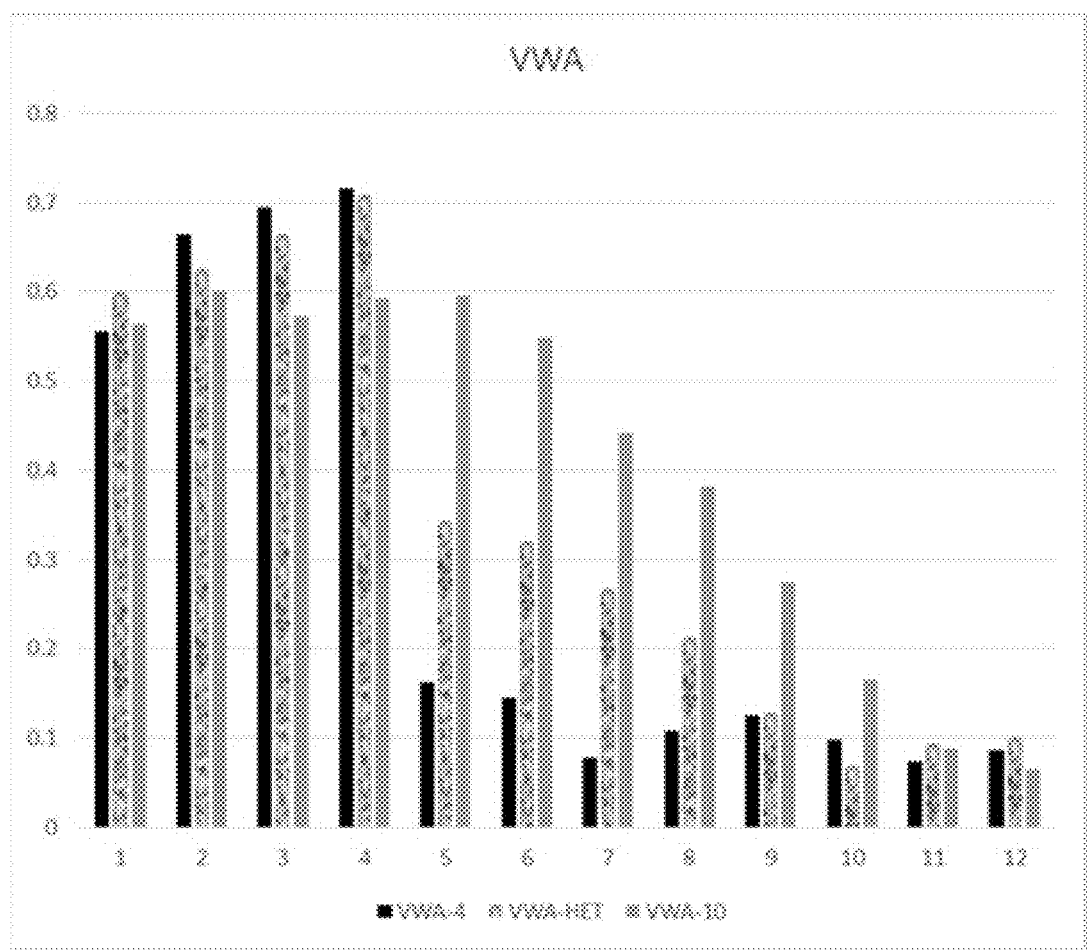

FIG. 4A provides a trace of the sequencing reaction and FIG. 4B depicts the data as a bar graph. The signal decay made it difficult to distinguish between the last positive signal and first negative for the VWA-Hetero sample. The positive signal indicating the presence of a "G" and thus a VWA repeating unit was strong for the VWA-4 sample and the VWA-hetero mixture until the VWA-4 template of the mixture was exhausted. FIG. 4B shows that the signal intensity of drops by half between cycle 4 and 5 which is when half the mixture (the VWA-4 template) was depleted.

C. Methods for Detecting Sex Determination STR Region Amelogenin

The sex determination allele amelogenin (AMEL) can also be detected using the method provided herein. The amelogenin allele on the Y chromosome includes a 6-base sequence [AAAGTG] that is deleted from the X chromosome. In this experiment, commercially available amelogenin PCR primers were used such as those available from Promega. Synthetic XX and XY chromosome templates were also used in the experiment. The sequencing reaction was performed similar to those described above. FIG. 5C shows an alignment of the allelic regions of the X and Y chromosomes (n.b. the sequences represent the sense strand that would be produced by extension of the sequencing primer used in this example). The position numbers arbitrarily correlate to the Y allele and are not intended to be limiting with regard to the origin of the allele differences as an insertion or deletion. Positions 5-10 don't actually exist in the X allele. Table 5 provides the steps of the reaction and Table 6 describes the reagents used.

TABLE 5

Sequencing Reaction for Amelogenin

| Amelogenin Step | Time (s) | |
| --- | --- | --- |
| Bind DNA | 300 | |
| Wash | 30 | |
| Incorporate AG | 45 | repeat |
| EDTA Wash | 90 | |
| Wash | 30 | |

TABLE 5-continued

Sequencing Reaction for Amelogenin

| Amelogenin Step | Time (s) |
| --- | --- |
| Examine T | 90 |
| Incorporate T | 45 |
| EDTA Wash | 90 |
| Wash | 30 |

For determining the presence of the amelogenin allele, "A" and "G" nucleotide bases were incorporated in the growing strand and the preselected "T" base was examined.

TABLE 6

Reagents for the Amelogenin Sequencing Reaction

| Wash Buffer | |
| --- | --- |
| Tris pH 8.0 | 30 mM |
| KCl | 160 mM |
| K$_2$ glutamate | 160 mM Glu- |
| Tween-20 | 0.01% (v/v) |
| b-ME | 1.0 mM |
| BSA | 100 µg/mL |
| T Incorporation | |
| Tris pH 8.0 | 30 mM |
| KCl | 160 mM |
| K$_2$ glutamate | 160 mM Glu- |
| Tween-20 | 0.01% (v/v) |
| b-ME | 1.0 mM |
| BSA | 100 ug/mL |
| MgCl$_2$ | 2.0 mM |
| Bsu DNA Pol | 68 U/mL |
| dTTP | 400 µM |
| T Examination | |
| Tris pH 8.0 | 30 mM |
| KCl | 160 mM |
| K$_2$ glutamate | 160 mM Glu- |
| Tween-20 | 0.01% (v/v) |
| b-ME | 1.0 mM |
| BSA | 100 µg/mL |
| Ni(II)SO$_4$ | 1 mM |
| Bsu DNA Pol | 68 U/mL |
| dTTP | 400 µM |
| EDTA Wash | |
| Tris pH 8.0 | 30 mM |
| KCl | 160 mM |
| EDTA | 1.0 mM |
| Tween-20 | 0.01% (v/v) |
| b-ME | 1.0 mM |
| BSA | 100 µg/mL |
| A-G Incorporation | |
| Tris pH 8.0 | 30 mM |
| KCl | 160 mM |
| K$_2$ glutamate | 160 mM Glu- |
| Tween-20 | 0.01% (v/v) |
| b-ME | 1.0 mM |
| BSA | 100 ug/mL |
| MgCl$_2$ | 2.0 mM |
| Bsu DNA Pol | 68 U/mL |
| dATP | 25 µM |
| dGTP | 25 µM |

Figure 5A:
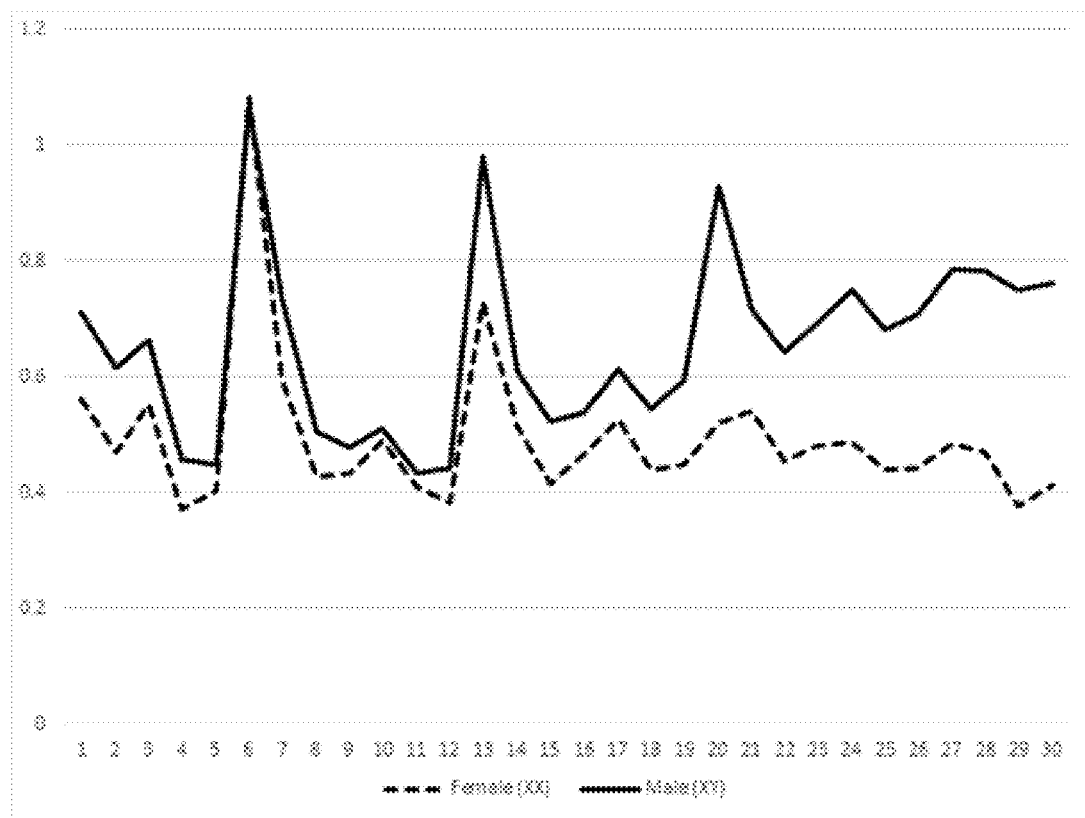
FIG. 5A and FIG. 5B are graphs showing results of an experiment for distinguishing indel alleles of the amelogenin loci in two different samples: (a) female sample containing a sequencing template having an X allele of the amelogenin locus (i.e. a deletion allele compared to the Y allele, indicated by adashed line or gray bar) and (b) a male sample containing a sequence template having a Y allele of the amelogenin locus (i.e. an insertion compared to the X allele, indicated by a solid line or black bar).
Figure 5B:
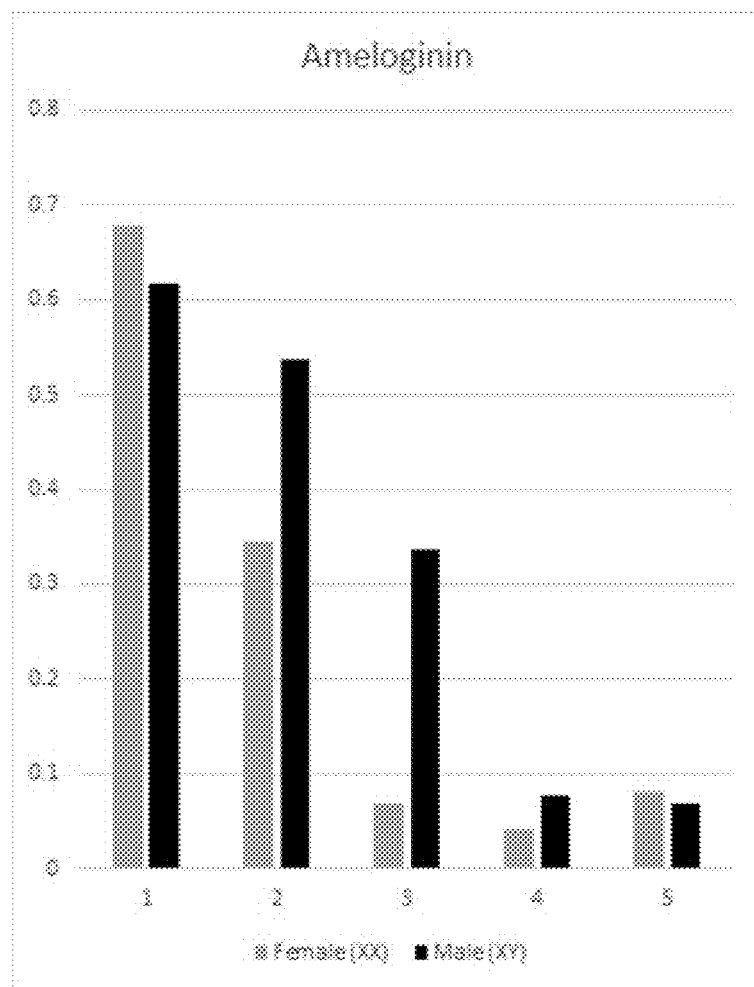

As evident from the sequences shown in FIG. 5C and the reaction cycles shown in Table 5, the X chromosome allele is expected to produce a count of 2 "T" signals. Specifically, the T at position 4 is expected to produce a signal in the first examination step and the triple T at positions 12-14 is expected to produce a signal in the second examination step. Note that the reaction does not proceed past position 15 since a C nucleotide is not used in any cycles of the sequencing reaction. In contrast, the Y chromosome allele is expected to produce a count of 3 "T" signals. Specifically, the first signal is expected to arise from position 4, the second signal from position 9, and the third signal from the triple T at positions 12-14. FIG. 5A shows a trace of the peaks from the sequencing reaction. FIG. 5B provides a bar graph of the results. Two peaks for the XX chromosome template represent the presence of a "T" and "TTT" outside of the amelogenin sequence variation, and thus absence of the 6-base pair unit. Three peaks for the XY chromosome represent its presence.

This example demonstrates that the signal counting methods set forth herein can be used for applications beyond identification and counting of sequence repeats. As shown here, different alleles of a particular locus can be distinguished based on differences in the pattern of signals produced when only a subset of nucleic acid base types are examined in a sequencing reaction. In cases where sequence variants are known or otherwise predictable, a sequence signature determined using the methods set forth herein can be adequate for distinguishing two sequences, whether or not the methods produce a sequence that is resolved in a positionally unambiguous way.

Example 2

Methods for Rapid Detection and Analysis of Complex Short Tandem Repeat (STR) Allelic Variations This example illustrates a method for counting the number of repeat units in a sample containing a complex STR region. Single repeating units such as TH01 can be examined using the method described above. For example, the process includes incorporating two bases (e.g., A and T) and examining with a third base (e.g., G). For more complex STR regions such as D21S11, a different method can be employed. Two of the D21S11 are shown in Table 7.

TABLE 7

| | D21S11 Variants | | | |
|---|---|---|---|---|
| Variant | Sequence | # of repeat units of section 1 | # of repeat units of section 2 | # of repeat units of section 3 |
| 26 | [TCTA]$_4$ [TCTG]$_6$ [TCTA]$_3$ TA | 4 | 6 | 18 |

TABLE 7-continued

| | D21S11 Variants | | | |
|---|---|---|---|---|
| Variant | Sequence | # of repeat units of section 1 | # of repeat units of section 2 | # of repeat units of section 3 |
| | [TCTA]$_3$ TCA [TCTA]$_2$ TCCA TA [TCTA]$_8$ | | | |
| 29.1 | [TCTA]$_4$ [TCTG]$_6$ [TCTA]$_6$ TCA [TCTA]$_2$ TCCA TA [TCTA]$_{11}$ | 4 | 6 | 21 |

For this allele, the repeating unit is examined in three parts or sections. First, the bases C and T are incorporated and the base type A is examined for 15 or more rounds or cycles. In section 1 of the method, 4 repeats should be counted for both variants (variants 26 and 29.1). In the following rounds, the method is modified such that the base type G is examined for 13 cycles or more. This should return 6 repeats in section 2 for both variants. Finally, the method is once again modified to incorporate the base type A and T and examine the base type C. For section 3, a sample containing variant 26 should give a count of 18 and a sample containing variant 29.1 should give a count of 21. As such, the identifying number of repeating units for variant 26 is 4-6-18 and the identifying number of repeating units for variant 29.1 is 4-6-21.

Depending on the STR allele, the repeating units can be divided into the appropriate number of sections. The specific bases used in the incorporating and examining steps can be adjusted and optimized for each of the sections. Described herein is a method of splitting complex STR alleles into different examination sections and assigning different incorporation and examination bases to each section as is necessary. This approach can be applied to numerous complex alleles such that many more variants can be resolved than by traditional separation methods.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of detecting a preselected signature in a nucleic acid, comprising:
   (a) incorporating a subset of nucleic acid base types into a primed nucleic acid to form an extended nucleic acid, wherein the subset of nucleic acid base types is complementary to at least one and no more than three nucleic acid base types in the primed nucleic acid, wherein incorporation of each of the individual nucleic acid base types is not detected among the subset of nucleic acid base types;
   (b) contacting the extended nucleic acid with a polymerase and a nucleotide with a preselected base type different from the nucleic acid base types in the subset of step (a);
   (c) detecting a ternary complex comprising the extended nucleic acid, the polymerase and the nucleotide with the preselected nucleic acid base type thereby detecting the preselected signature, wherein the nucleotide with the preselected base type is prevented from incorporating into the extended nucleic acid during the detecting;
   (d) incorporating, after step (b), the nucleotide with the preselected based type into the extended nucleic acid;
   (e) repeating steps (a) and (b) at least one time after step (d); and
   (f) determining a number of times the preselected nucleic acid base type is detected to determine a number of times the preselected signature occurs.

2. The method of claim 1, wherein the primed nucleic acid comprises a plurality of repeat units.

3. The method of claim 2, wherein the number of times the ternary complex is detected is the number of repeat units within the primed nucleic acid.

4. The method of claim 1, further comprising a wash step prior to step (b).

5. The method of claim 1, wherein the nucleotide comprising the preselected nucleic acid base type in step (b) is labeled.

6. The method of claim 5, wherein the subset of nucleic acid base types comprises unlabeled nucleic acid base types.

7. A method of distinguishing target sequences, comprising:
   (a) providing a primed nucleic acid that comprises a primer hybridized to a template strand, wherein the template strand comprises a candidate sequence selected from at least two known target sequences;
   (b) contacting the primed nucleic acid with a polymerase and a subset of nucleic acid base types, whereby the subset of nucleic acid base types incorporates into the primer to produce an extended primed nucleic acid;
   (c) contacting the extended primed nucleic acid with a polymerase and a preselected nucleic acid base type different from the subset of nucleic acid base types, whereby a ternary complex forms if the preselected nucleic acid base type is the next correct nucleotide for the extended primed nucleic acid product, and wherein the ternary complex is stabilized to prevent incorporation of the preselected nucleic acid base type into the extended primed nucleic acid;
   (d) acquiring a signal produced by the ternary complex; and
   (e) repeating (b) through (d) at least one time to obtain a series of signals, wherein the series of signals comprises a signature that identifies the candidate sequence.

8. The method of claim 7, wherein the two known target sequences are different alleles of a single locus, and wherein one of the alleles is identical to or complementary to the preselected nucleic acid base type.

9. The method of claim 7, wherein the candidate sequence comprises an indel comprising at least one nucleic acid base type that is identical to or complementary to the preselected nucleic acid base type.

10. The method of claim 7, further comprising performing the method for a second primed nucleic acid that comprises a primer hybridized to a second template strand, wherein the template strand comprises a second candidate sequence selected from the at least two known target sequences, thereby obtaining a second set of signals.

11. The method of claim 10, further comprising comparing the second series of signals to the series of signals acquired in (d), thereby distinguishing the at least two known target sequences.

12. The method of claim 7, further comprising (f) repeating (b) and (c) at least one time using a second subset of nucleic acid base types that differs from the subset of nucleic acid base types, whereby the second subset of nucleic acid base types incorporates into the extended primed nucleic acid to produce a further extended primed nucleic acid, and whereby a second ternary complex forms for the further extended primed nucleic acid product; and (g) acquiring a second signal produced by the second ternary complex, wherein the first and second signals comprises a signature that distinguishes the target sequence from another of the at least two known target sequences.

13. The method of claim 12, wherein the first preselected nucleic acid base type and the second preselected nucleic acid base type are complementary to different nucleic acid base types in the template strand.

14. The method of claim 12, wherein the first preselected nucleic acid base type and the second preselected nucleic acid base type are complementary to the same nucleic acid base type in the template strand.

15. The method of claim 7, wherein the same type of polymerase is used in step (b) and step (c).

16. A method of determining the presence of a repeat unit within a nucleic acid region in a sample, comprising:

(a) providing a primed nucleic acid that comprises a primer hybridized to a template strand with at least one repeat unit downstream of the primer;

(b) contacting the primed nucleic acid with a polymerase and a subset of nucleic acid base types, whereby the subset of nucleic acid base types incorporates into the primer to produce an extended primed nucleic acid;

(c) contacting the extended primed nucleic acid with a polymerase and a preselected nucleic acid base type different from the subset of nucleic acid base types, whereby a ternary complex forms if the preselected nucleic acid base type is the next correct nucleotide for the extended primed nucleic acid product, and wherein the ternary complex is stabilized to prevent incorporation of the preselected nucleic acid based type into the extended primed nucleic acid; and (d) detecting the ternary complex while preventing incorporation of the preselected nucleic acid base type into the extended primed nucleic acid, thereby determining the presence of the repeat unit within the nucleic acid region.

17. The method of claim 16, further comprising the steps of:

(f) repeating steps (b), (c), (d), and (e) at least one time until the ternary complex is no longer detected; and (g) determining that the number of repeat units within the nucleic acid region is the same as the number of times the ternary complex is detected.

18. The method of claim 1, wherein the subset of nucleic acid base types is complementary to at least two and no more than three nucleic acid base types in the primed nucleic acid.

19. The method of claim 1, wherein the subset of nucleic acid base types is complementary to at least three and no more than three nucleic acid base types in the primed nucleic acid.

20. The method of claim 1, wherein the nucleic acid base types that are incorporated in step (a) do not comprise exogenous labels.

* * * * *

UNITED STATES PATENT AND TRADEMARK OFFICE
CERTIFICATE OF CORRECTION

PATENT NO. : 10,253,352 B2
APPLICATION NO. : 15/354941
DATED : April 9, 2019
INVENTOR(S) : Michael Nguyen and Eugene Tu Page 1 of 1

It is certified that error appears in the above-identified patent and that said Letters Patent is hereby corrected as shown below:

In the Claims

Column 53, Line 48, "after step (b)" should read:
-- after step (c) --

Column 53, Line 49, "preselected based type" should read:
-- preselected base type --

Column 56, Line 17, "(f) repeating steps (b), (c), (d), and (e)" should read:
-- (e) repeating steps (b), (c), and (d) --

Column 56, Line 19, "(g)" should read:
-- (f) --

Signed and Sealed this
Eleventh Day of June, 2019

Andrei Iancu
*Director of the United States Patent and Trademark Office*